United States Patent [19]

Yoon

[11] Patent Number: 5,782,800
[45] Date of Patent: *Jul. 21, 1998

[54] EXPANDABLE MULTIFUNCTIONAL MANIPULATING INSTRUMENTS FOR VARIOUS MEDICAL PROCEDURES AND METHODS THEREFOR

[76] Inventor: InBae Yoon, 2101 Highland Ridge Dr., Phoenix, Md. 21131

[ * ] Notice: The portion of the term of this patent subsequent to May 15, 2015, has been disclaimed.

[21] Appl. No.: 768,239

[22] Filed: Dec. 17, 1996

Related U.S. Application Data

[60] Continuation of Ser. No. 441,465, May 15, 1995, Pat. No. 5,656,013, which is a division of Ser. No. 249,116, May 25, 1994, Pat. No. 5,514,091, which is a continuation-in-part of Ser. No. 596,937, Oct. 15, 1990, abandoned, which is a continuation-in-part of Ser. No. 222,776, Jul. 22, 1988, abandoned.

[51] Int. Cl.$^6$ .................................................. A61M 31/00
[52] U.S. Cl. .......................... 604/54; 604/101; 606/191; 600/207
[58] Field of Search .............................. 604/96, 101, 264, 604/280, 54; 606/191, 192, 193, 194, 190; 600/201, 207, 226, 215

[56] References Cited

U.S. PATENT DOCUMENTS 5,197,971  3/1993  Bonutti ............................ 606/192
5,246,421  9/1993  Saab ................................. 604/96

Primary Examiner—Corrine M. McDermott

[57] ABSTRACT

An expandable multifunctional instrument for performing various diverse operative procedures includes an elongate distensible member having a distal end for being introduced in an anatomical cavity via a relatively small size anatomical opening and being movable from a non-distended position facilitating introduction through the anatomical opening to a distended position wherein the cross-sectional size of the distensible member is increased and a plurality of collars disposed on portions of the distensible member for constraining movement of the distensible member portions to the distended position. The collars are movably mounted on the distensible member for adjusting the location and size of unconstrained distensible portions of the distensible member adjacent the collars. A method of performing an operative procedure in an anatomical cavity includes the steps of introducing a distal end of an elongate distensible member in the anatomical cavity through a relatively small size anatomical opening with the distensible member in a non-distended position, moving the distensible member from the non-distended position to a distended position and constraining selected portions of the distensible member against movement to the distended position to selectively contour the distensible member in the distended position to have a plurality of protuberances.

6 Claims, 25 Drawing Sheets

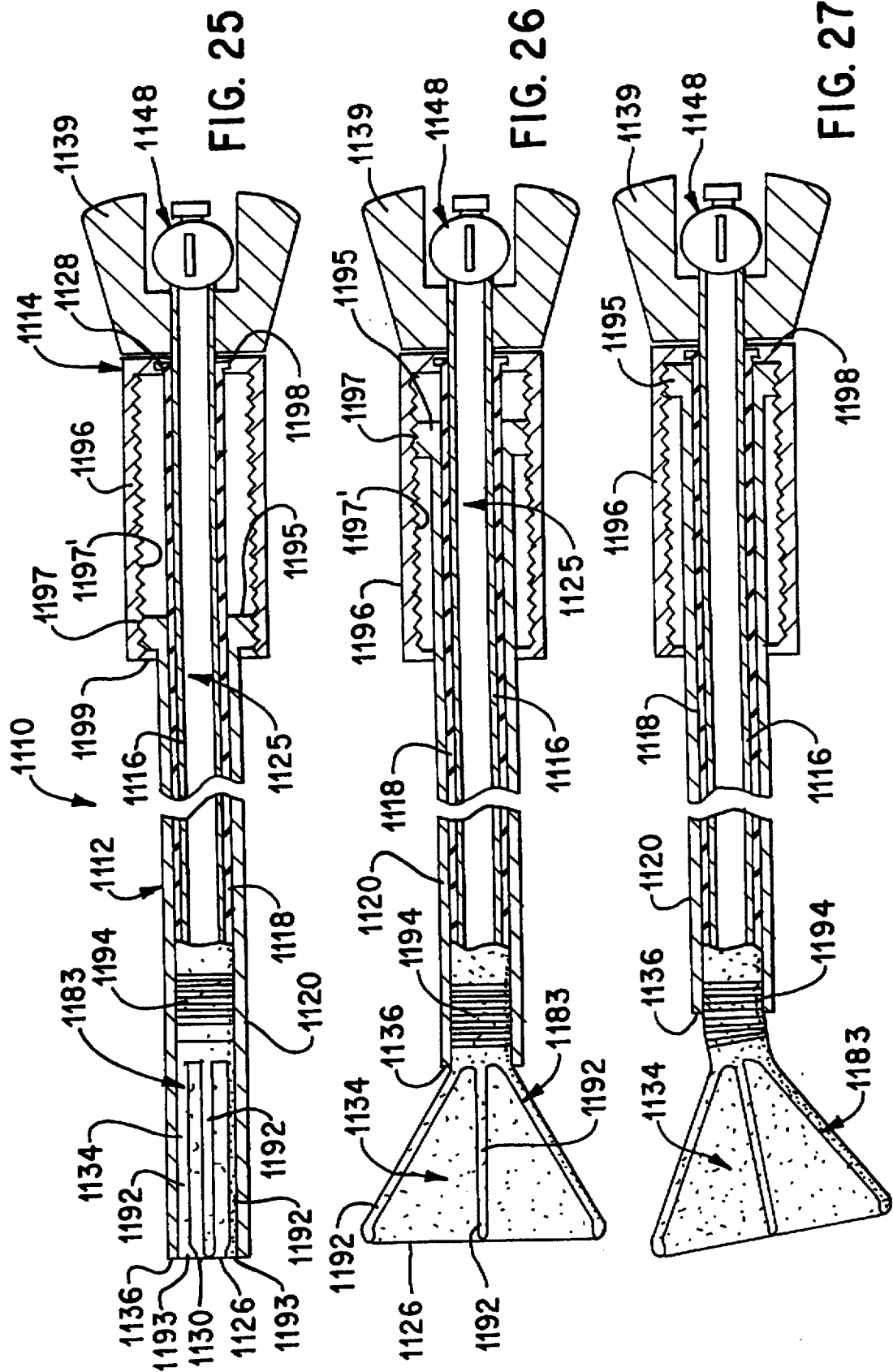

EXPANDABLE MULTIFUNCTIONAL MANIPULATING INSTRUMENTS FOR VARIOUS MEDICAL PROCEDURES AND METHODS THEREFOR

CROSS-REFERENCE TO RELATED APPLICATIONS

This application is a continuation of prior pending application Ser. No. 08/441,465, filed May 15, 1995 now U.S. Pat. No. 5,656,013, which is a divisional of prior application Ser. No. 08/249,116, filed May 25, 1994 now U.S. Pat. No. 5,514,091 which is a continuation-in-part of application Ser. No. 07/596,937 filed Oct. 15, 1990 now abandoned, which is a continuation-in-part of prior application Ser. No. 07/222, 776 filed Jul. 22, 1988 and now abandoned. The foregoing patent application are incorporated herein by reference.

BACKGROUND OF THE INVENTION

1. Field of the Invention

The present invention relates to multifunctional medical instruments for performing various diverse procedures in anatomical cavities and, more particularly, to multifunctional instruments having distal ends for being introduced at the anatomical cavities from externally thereof via relatively small size natural or artificial openings in walls of the anatomical cavities and to methods therefor.

2. Description of the Prior Art

It is often necessary to perform various medical procedures in anatomical cavities, such as blood vessels and cranial, chest, uterine, pelvic and abdominal cavities, or on tissue or organ structures within anatomical cavities. It is desirable in many cases to perform such procedures via relatively small size natural or artificial openings in walls of the anatomical cavities to avoid the need for large incisions and accompanying trauma. Accordingly, endoscopic procedures, otherwise known as closed or least invasive procedures, have become extremely popular for use in performing various medical procedures in anatomical cavities. In endoscopic procedures, distal ends of instruments are introduced at the anatomical cavities from externally thereof via relatively small size artificial or natural openings in walls of the anatomical cavities allowing various medical procedures to be performed with the instruments under endoscopic visualization. Endoscopic procedures have many advantages over open procedures, which require relatively large incisions, including reduced trauma and recovery time for the patient.

In view of the advantages of endoscopic procedures there is a great demand to expand the procedures that can be performed endoscopically; however, expansion of endoscopic techniques into many areas has been limited due to the lack of medical instruments available for performing many procedures in anatomical cavities via relatively small size openings. In addition, many medical instruments that are presently available for use in endoscopic procedures are themselves limited in that the instruments can perform only a single procedure or function.

Accordingly, there is a great need for multifunctional instruments for being introduced at anatomical cavities via relatively small size artificial or natural openings in walls of the anatomical cavities to perform a variety of diverse medical procedures, such as manipulating tissue, separating adhering tissue (lysis of adhesion), tissue dissection, displacing healthy tissue from tissue to be treated, collecting tissue and/or fluid samples, stabilizing instruments introduced at the anatomical cavities, aspirating or absorbing body fluids, irrigating, electrosurgery, laser surgery and sealing or closing anatomical openings.

SUMMARY OF THE INVENTION

Accordingly, it is a primary object of the present invention to overcome the aforementioned disadvantages of prior art medical instruments.

Another object of the present invention is to provide a single medical instrument for performing various diverse procedures in anatomical cavities via relatively small size artificial or natural openings in walls of the anatomical cavities.

An additional object of the present invention is to provide a method of performing endoscopic procedures in an anatomical cavity wherein organ structures within the anatomical cavity are manipulated with the use of an inflated balloon such that organ structures can be separated or elevated relative to one another and the anatomical cavity wall can be separated from organ structures within the anatomical cavity. As used herein, "organ structure" and "tissue" are meant to be synonymous and to include complete walls or parts thereof.

A further object of the present invention is to provide a multifunctional instrument including an elongate distensible member having a distal end for being introduced at an anatomical cavity and being movable from a non-distended position to a distended position and one or more collars disposed on the distensible member to prevent movement of the distensible member to the distended position along the collars for controlling the shape of the distensible member in the distended position in accordance with a procedure to be performed in the anatomical cavity.

An additional object of the present invention is to provide a multifunctional instrument including an elongate member having a distal end for being introduced at an anatomical cavity and being movable between a non-expanded position wherein the elongate member has a first cross-sectional size and an expanded position wherein the elongate member has a second cross-sectional size greater than the first size and a plurality of collars disposed over portions of the elongate member to constrain movement of the elongate member portions toward the expanded position, the collars being movable along the elongate member to change the location of the constrained elongate member portions to obtain a desired shape for the elongate member in the expanded position.

It is also an object of the present invention to provide a multifunctional instrument including an elongate member having a distal end for being introduced at an anatomical cavity, a plurality of expandable portions individually, selectively movable between a non-expanded position and an expanded position and one or more non-expandable portions along which movement of the elongate member to the expanded position is constrained.

Yet another object of the present invention is to provide a multifunctional instrument including an elongate member having a distal end for being introduced at an anatomical cavity and one or more expandable portions movable between a non-expanded position and an expanded position wherein the one or more expandable portions has a predetermined configuration in accordance with a medical procedure to be performed with the one or more expandable portions.

A still further object of the present invention is to provide a method of performing an operative procedure in an anatomical cavity including the steps of introducing a distal end of an elongate distensible member in an anatomical cavity with the distensible member in a non-distended position, constraining selected portions of the distensible member against movement from the non-distended position to a distended position to selectively contour the distensible member to have a plurality of protuberances for engaging anatomical tissue in the distended position.

Some of the advantages of the present invention are that the types of procedures that can be performed endoscopically can be greatly expanded, various procedures can be performed in anatomical cavities with the multifunctional instruments of the present invention with the instruments stabilized relative to the anatomical cavities, the multifunctional instruments can provide a passage for introduction of various additional instruments in the anatomical cavities, the size, shape and position of the expandable portions are easily adjustable in accordance with procedural use, the configuration of the expandable portions in the expanded position can be controlled in accordance with procedural use, selective, controlled individual distension of the expandable portions allows the size and rigidity of the expandable portions in the expanded position to be individually controlled and allows selected expandable portions to remain undistended during use, and a wide range of medical or operative procedures can be performed via small size anatomical openings, such procedures including tissue or organ structure manipulation, separation of adhering tissue (lysis of adhesion), dissection of tissue, electrosurgical and laser procedures, anatomical cell collection, closing off or sealing anatomical openings and enhancing access or space at operative sites in the anatomical cavities.

These and other objects, advantages and benefits are realized with instruments of the present invention which permit inflated balloons to be used to separate organ structures within an anatomical cavity and to separate anatomical cavity walls from organ structures within the anatomical cavity as well as with multifunctional instruments of the present invention including a distensible elongate member having a distal end for being introduced in an anatomical cavity and being movable from a non-distended position wherein the distensible member has a first cross-sectional size to facilitate introduction in the anatomical cavity through a relatively small size anatomical opening and a distended position wherein the distensible member has a second cross-sectional size larger than the first cross-sectional size and one or more collars disposed on portions of the distensible member for constraining movement of the distensible member portions toward the distended position whereby unconstrained portions of the distensible member adjacent the collars define distensible portions forming enlargements or protrusions in the distended position. The one or more collars are movably mounted on the distensible member to adjust the location and size of the distensible portions in accordance with procedural use. The distensible portions can be selectively, individually moved between the distended position and the non-distended position to selectively, individually control the size and/or rigidity of the distensible portions in the distended position and to permit selective distensible portions to remain distended during use.

A method of performing an operative procedure according to the present invention includes the steps of introducing a distal end of an elongate distensible member in an anatomical cavity through a relatively small size anatomical opening with the distensible member in a non-distended position, moving the distensible member from the non-distended position to a distended position wherein the cross-sectional size of the distensible member is increased, constraining selected portions of the distensible member against movement to the distended position to selectively contour the distensible member to have a plurality of protuberances for engaging anatomical tissue in the distended position in accordance with the operative procedure to be performed and performing an operative procedure in the anatomical cavity with the multifunctional instrument in the distended position.

Other objects and advantages of the present invention will become apparent from the following description of the preferred embodiments taken in conjunction with the accompanying drawings wherein like parts in each of the several figures are identified by the same reference characters.

BRIEF DESCRIPTION OF THE DRAWINGS

FIG. 25 is a broken side view, partly in section of a further embodiment of an expandable multifunctional instrument according to the present invention with the expandable portion thereof in the non-expanded position.

FIG. 26 is a broken side view, partly in section, of the expandable multifunctional instrument of FIG. 25 with the expandable portion thereof in the expanded position.

FIG. 27 is a broken side view, partly in section, of the expandable multifunctional instrument of FIG. 25 with the expandable portion thereof in an expanded, offset position.

DESCRIPTION OF THE PREFERRED EMBODIMENTS

Figure 1:
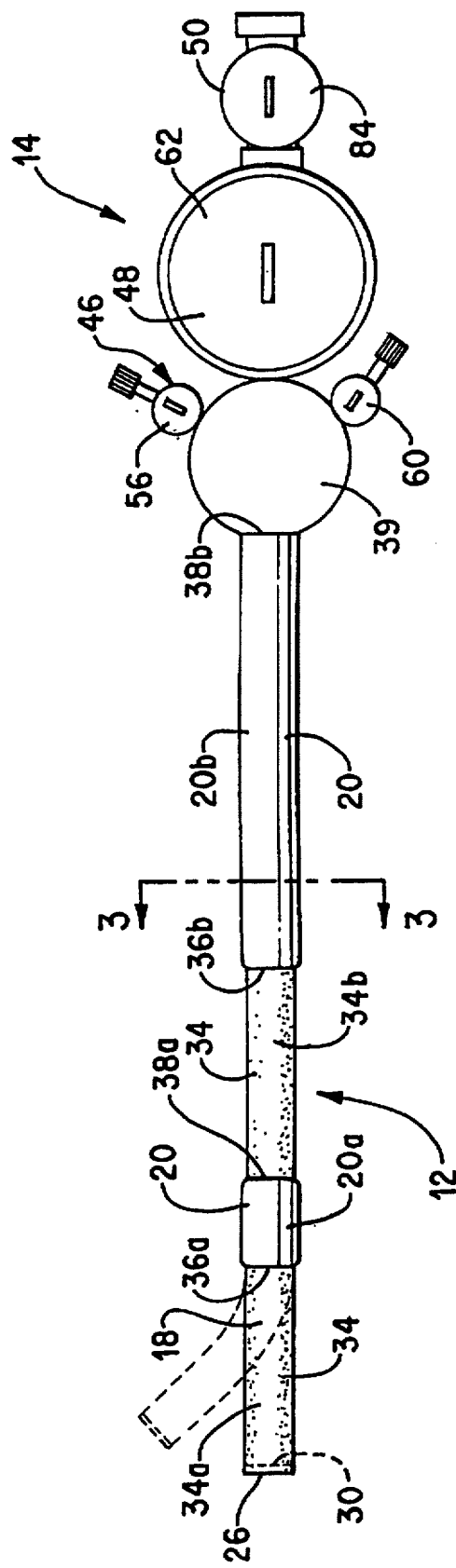
FIG. 1 is a side view of an expandable multifunctional instrument according to the present invention.
Figure 2:
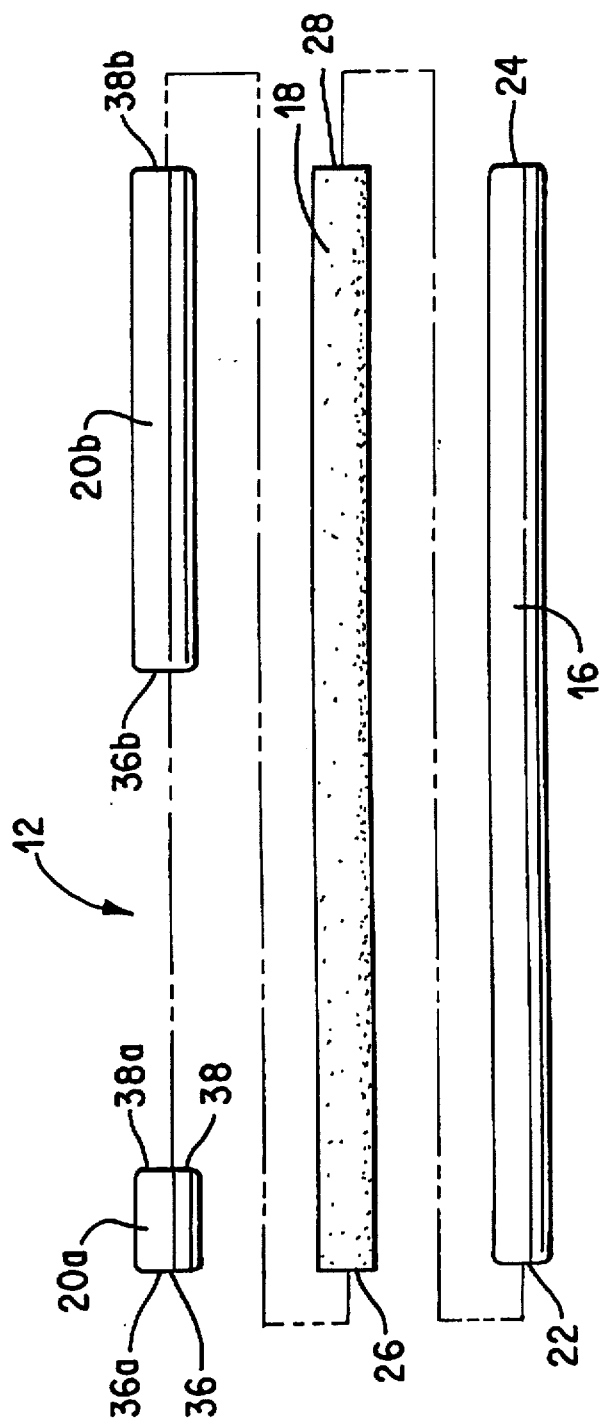
FIG. 2 is an exploded side view of the body assembly for the expandable multifunctional instrument of FIG. 1.
Figure 3:
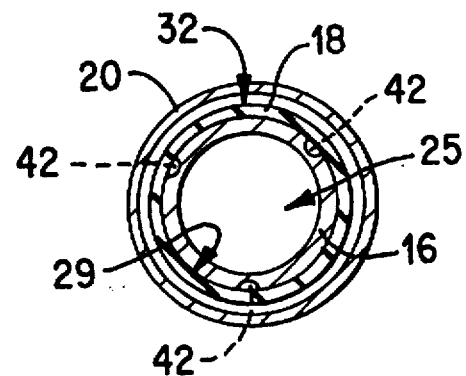
FIG. 3 is a cross-sectional view of the body assembly taken along line 3—3 of FIG. 1 prior to fluid being supplied between the middle and inner members.
Figure 15:
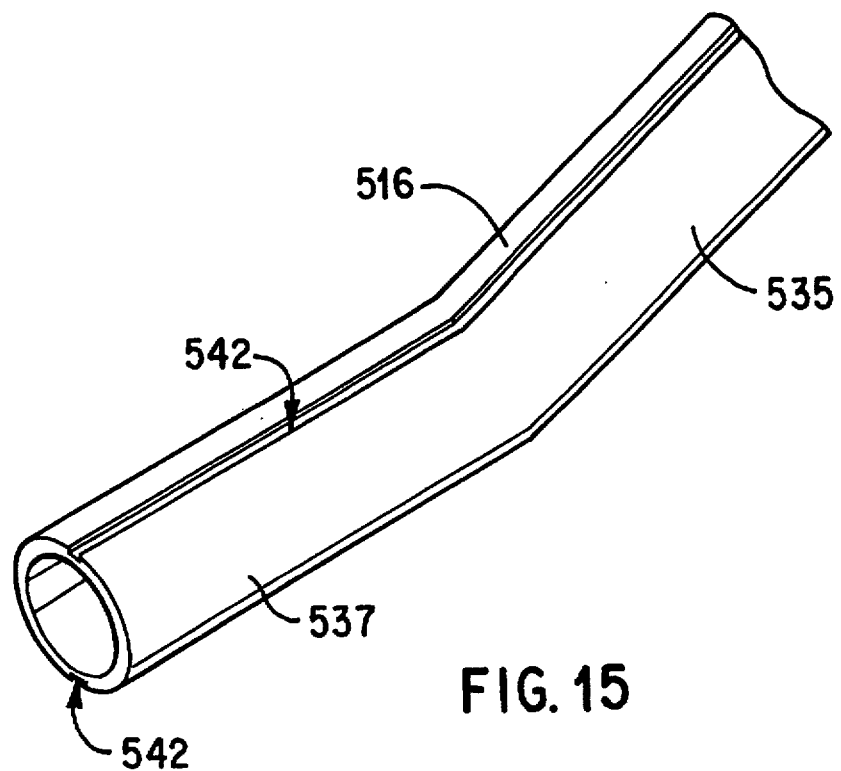
FIG. 15 is a broken perspective view of the inner member for the expandable multifunctional instrument of FIG. 14.

An expandable multifunctional instrument 10 according to the present invention, as illustrated in FIG. 1, includes a body assembly 12 and a head assembly 14 mounting a proximal end of body assembly 12. Body assembly 12, as best shown in FIGS. 2 and 3, includes an elongate inner member 16, a middle member 18 receiving inner member 16 and one or more outer collars or spacers 20 disposed on middle member 18, two collars 20a and 20b being shown for instrument 10. Inner member 16 can be made of any suitable rigid, semi-rigid, flexible or bendable medical grade material, such as metal or plastic, and can be solid, hollow or tubular or formed with an internal passage, or partly hollow or tubular in accordance with procedural use. The inner member 16 can have any desirable cross-sectional configuration including cylindrical or tubular configurations; and, as shown, inner member 16 is made of a substantially cylindrical length of metal or plastic tubing. Inner member 16 can be straight as shown in FIG. 2, rigidly curved, bent or angled as shown in FIG. 15, or the inner member can be bent or curved during use as shown in dotted lines in FIG. 1 depending on procedural use. Inner member 16 includes a distal end 22, a proximal end 24 and, where the inner member is tubular or hollow or formed with an internal passage, a lumen or passage 25 extending longitudinally between the distal and proximal inner member ends, the lumen 25 being shown in FIG. 3.

Middle member 18 is designed to be movable between a non-distended, non-expanded or collapsed position or condition wherein the middle member 18 has a first cross-sectional size and a distended or expanded position or condition wherein the middle member has a second cross-sectional size larger than the first cross-sectional size. The middle member 18 includes a distal end 26, a proximal end 28 and a lumen or passage 29 for receiving the inner member 16. The middle member 18 can be made of an expandable, distensible, collapsible, flexible, resilient, stretchable or elastic material, such as medical grade silicone or latex rubber or sponge, or of a non-elastic, non-stretchable, rigid material. The outer surface of the middle member can include a mesh or fibers providing a non-smooth, roughened surface for adhering to or gripping tissue. As shown in FIGS. 1 and 2, middle member 18 is in the nature of an expandable or inflatable tubular membrane or balloon made of stretchable, elastic material; however, the middle member 18 can be made of non-stretchable, non-elastic material and can have any desirable cross-sectional configuration including various preformed predetermined shapes as will be explained further below. The middle member 18 can be made of an electrically conductive material or can include electrically conductive fibers or an electrically conductive spine for electrical coagulation or cauterization of tissue depending on procedural use.

Figure 19:
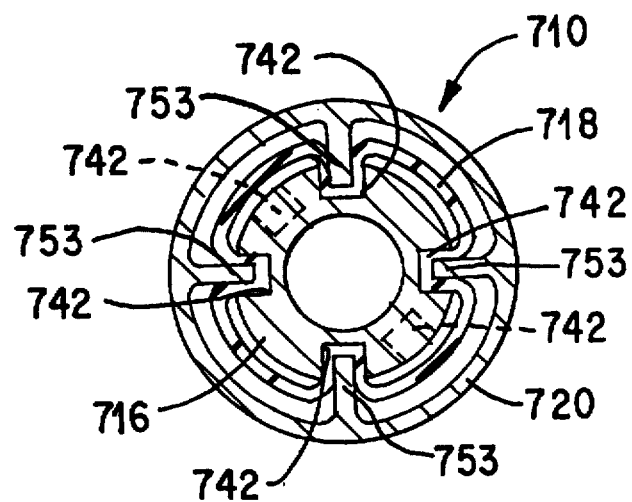
FIG. 19 is a cross-sectional view of another modification of an expandable multifunctional instrument according to the present invention.

Depending on the size, configuration and materials of the middle member, the middle member 18 can be assembled over the inner member 16 with a snug or tight fit as shown in FIG. 3 or with a loose fit as shown in FIG. 19. As shown in FIG. 3, middle member 18 for instrument 10 is configured to fit snugly over inner member 16 with little or no circumferential gap or space therebetween to minimize the profile of body assembly 12 in the non-expanded position to facilitate introduction in an anatomical cavity via a relatively small size natural or artificial anatomical opening. Accordingly, the middle member 18 can stretch or "give" to fit over or receive the inner member 16 with a snug fit, in which case the middle member lumen 29 can be smaller in size in a non-stretched state than the outer diameter or size of inner member 16, or the lumen 29 can be the same or substantially the same size as inner member 16 to snugly receive the inner member 16 without stretching.

Figure 5:
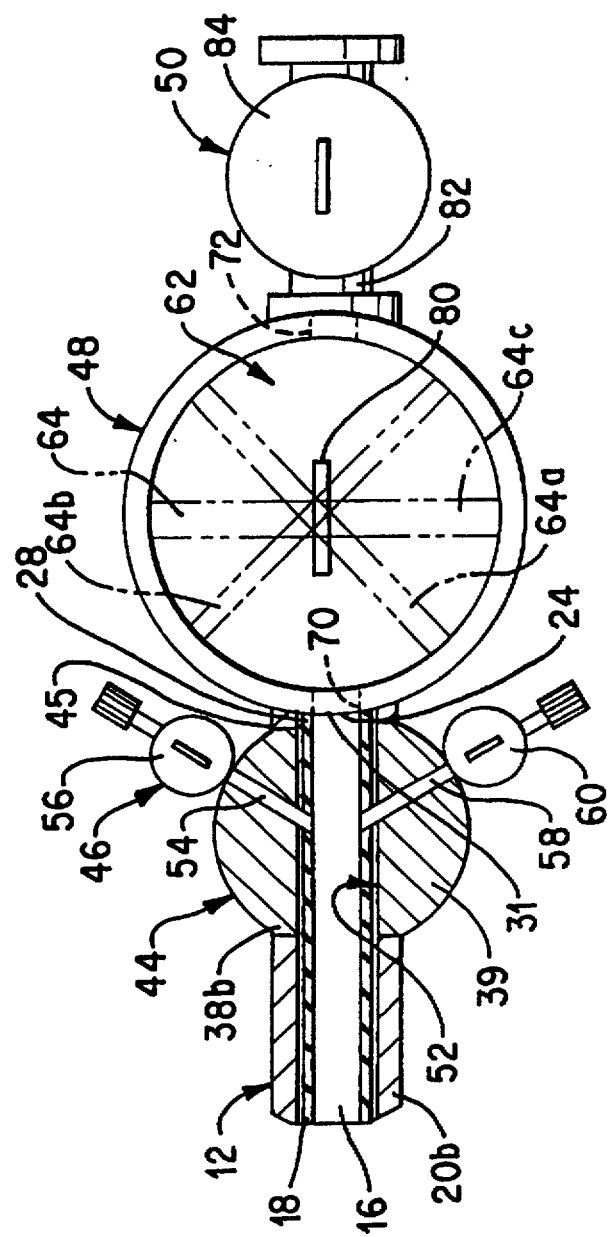
FIG. 5 is a broken side view, partly in section, of the head assembly for the expandable multifunctional instrument of FIG. 1.

With the inner member 16 disposed in the middle member 18, an actual initial space or a potential space for fluid flow will be defined between the middle member 18 and the inner member 16 depending on whether the middle member 18 fits loose or snug on the inner member 16. Where the middle member 18 fits snug or tight on the inner member 16 as in multifunctional instrument 10, a potential space for fluid flow is defined between the middle member 18 and the inner member 16 due to the elasticity of middle member 18. Where the middle member 18 fits loose on the inner member 16 and where the collars 20 fit loose upon the middle member 18, an actual initial space will be defined between the middle member and the inner member as explained further below. The actual or potential space is closed off or sealed by distal and proximal seals to form a closed fluid path. As shown in FIG. 1, the middle member 18 is closed off or sealed at the distal end thereof such as being secured or sealed to the inner member 16 at a circumferential distal seal 30. The middle member 18 is closed off or sealed at the proximal end thereof; and as shown in FIG. 5, the inner member proximal end 24 and the middle member proximal end 28 are both mounted to valve 62 of head assembly 14 with a wall of valve 62 forming a circumferential proximal seal 31. The distal and proximal seals can be formed by the middle member itself or any other structure of the instrument as well as by securing or sealing the middle member 18 to the inner member 16. The distal and proximal seals 30 and 31, respectively, can be disposed at various locations along the length of the instrument 10 in accordance with the length desired for the closed fluid path, i.e. the length along which the actual or potential space is sealed. The proximal and distal seals 30 and 31 can be formed in many various ways, such as with adhesives, mechanically with the use of seal members and by structure of the instrument 10.

Collars 20 are configured to be disposed over the assembly of middle member 18 and inner member 16 and are preferably made of a suitable rigid, semi-rigid, flexible or bendable medical grade material of sufficient rigidity and/or strength to control, constrain or limit expansion or distension of the middle member 18 along the length of the collars when fluid is supplied between the middle member 18 and the inner member 16. Collars 20 can have any desirable cross-sectional configuration, such as tubular or cylindrical, C-shaped and U-shaped configurations, defining a lumen or passage 32 allowing passage therethrough by the assembly of middle member 18 and inner member 16. Collars 20 have a size and configuration and are arranged on the assembly of middle member 18 and inner member 16 to define one or more non-distensible or non-expandable portions along the collars 20 along which expansion or distension of middle member 18 is constrained, limited or controlled and one or more expandable or distensible portions 34 adjacent the collars 20, the expandable portions 34 being disposed along the closed fluid path between the distal and proximal seals 30 and 31. As shown in FIGS. 1 and 2, collars 20a and 20b have longitudinally straight, tubular configurations with lumens 32 allowing passage therethrough by the assembly of middle member 18 and inner member 16 and are arranged on the middle member 18 to define two non-expandable portions along the length of the collars 20a and 20b and two expandable portions 34a and 34b adjacent the collars 20a and 20b, respectively, and disposed between seals 30 and 31. The cross-sectional size and configuration of collars 20a and 20b can be the same or different; and, where the collars are to be introduced in an anatomical cavity via an opening in a wall of the anatomical cavity and/or are to be positioned to extend along the anatomical opening, the cross-sectional size of the collars can be selected in accordance with the cross-sectional size of the anatomical opening to facilitate passage of the collars therethrough and/or to form a seal with the anatomical opening.

Figure 11:
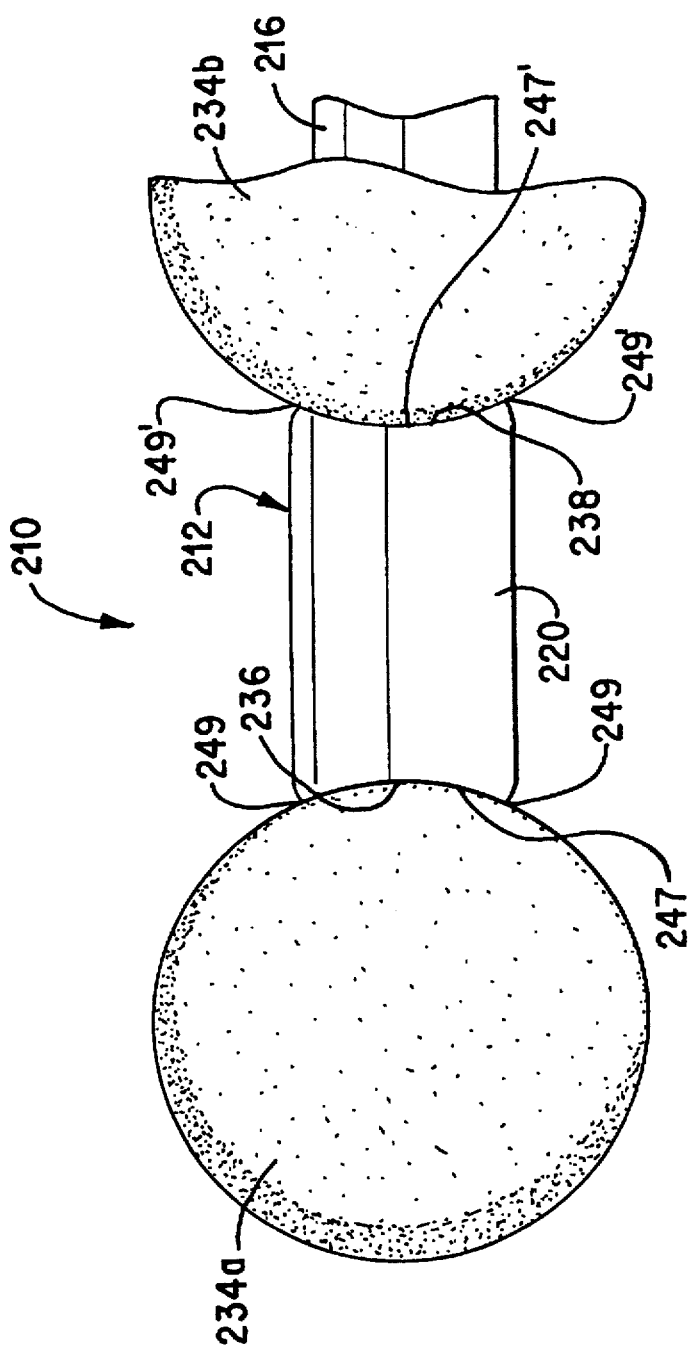
FIG. 11 is a broken side view of a modification of an expandable multifunctional instrument according to the present invention.

Collars 20 have forward edges 36 and rearward edges 38 with a length between the forward and rearward edges. Collars 20 can have the same length or different lengths, and the lengths of the collars can be selected to obtain a desired size, separation and position for expandable portions 34. The forward and rearward edges 36 and 38 can be disposed in planes parallel to one another and transverse or perpendicular to a longitudinal axis of the collars as shown in FIGS. 1 and 2, or the forward and rearward edges can have a concave configuration curving inwardly from the parallel, transverse planes as shown in FIG. 11. As shown in FIG. 1, collar 20a is arranged on the assembly of middle member 18 and inner member 16 with the forward edge 36a thereof disposed proximally of distal seal 30 a distance corresponding to a desired length for expandable portion 34a. Collar 20b is arranged on the assembly of middle member 18 and inner member 16 with forward edge 36b thereof spaced proximally from rearward edge 38a of collar 20a a distance corresponding to a desired length for expandable portion 34b with the length of collar 20a corresponding to the desired separation distance between expandable portions 34a and 34b. Where no expandable portion is desired proximally of expandable portion 34b, the rearward edge 38b of collar 20b can terminate at or within the head assembly 14. As shown in FIGS. 1 and 5, rearward edge 38b of collar 20b abuts a handle 39 of head assembly 14 such that no expandable portion is defined proximally of expandable portion 34b. By providing a plurality of collars 20 of different lengths and different cross-sectional shapes and sizes, collars can be selected for assembly on the middle member in accordance with the size of the anatomical opening and to obtain a desired number, size, position and separation for the expandable portions in accordance with procedural use.

Figure 4:
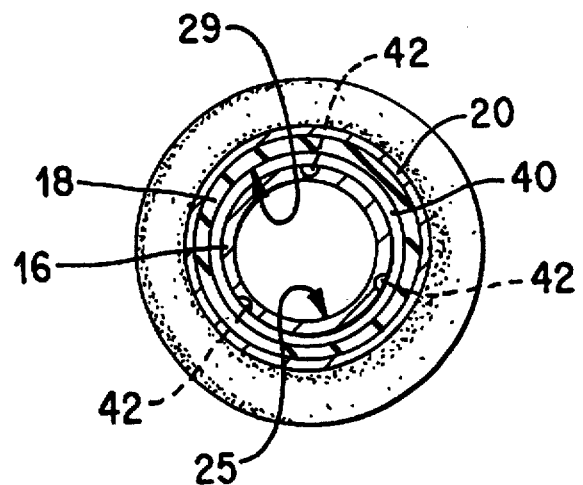
FIG. 4 is a cross-sectional view of the body assembly taken along line 3—3 of FIG. 1 with fluid supplied between the middle and inner members.
Figure 16:
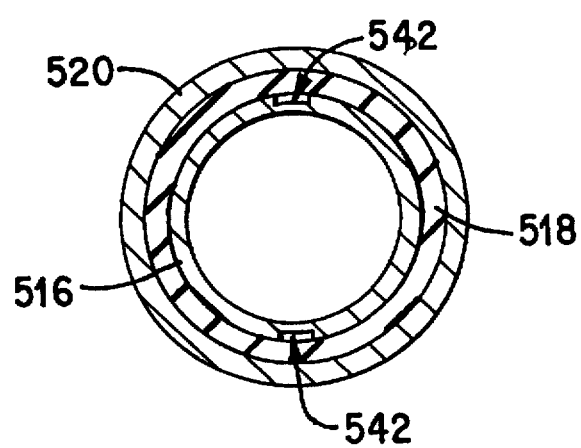
FIG. 16 is a cross-sectional view of the expandable multifunctional instrument of FIG. 14.

The collars 20 can be disposed on the assembly of middle member 18 and inner member 16 with a somewhat loose fit as shown in FIG. 3 or with a snug fit as shown in FIG. 16. As illustrated in FIG. 3, collars 20 have an inner diameter or size slightly greater than the outer diameter or size of the assembly of middle member 18 and inner member 16 such that the collars 20 do not fit tight upon the middle member 18. Accordingly, fluid supplied between the inner member 16 and the middle member 18, i.e. to the actual initial space or to the potential space, via head assembly 14 will move middle member 18 toward inner surfaces of the collars creating an actual gap or space from the potential space or increasing the size of the actual initial space to permit fluid flow along, through or past the collars 20. As shown for instrument 10 in FIG. 3, prior to fluid being supplied to the potential space, the middle member 18 remains tight against the inner member 16. As shown in FIG. 4, once fluid has been supplied to the potential space, middle member 18 is moved radially outwardly toward the inner surface of collar 20 creating an actual space 40 between the middle member 18 and the inner member 16 allowing fluid flow along the collar 20. It will be appreciated that where there is an actual initial space between the middle member and the inner member and a loose fit of the collar upon the assembly of the middle member and the inner member, the size of the actual initial space will be increased when the middle member is moved outwardly toward the inner surface of the collar upon supply of fluid to the initial space. A slightly loose fit for collars 20 allows the collars 20 to be moved or slid longitudinally along the assembly of middle member 18 and inner member 16 for assembly thereon, for removal therefrom and to adjust the position of the collars 20 to change the size, separation and/or position of expandable portions 34. At least the inner surfaces of the collars can be made of a slippery material to facilitate movement of the collars along the assembly of the middle member and the inner member without tearing, snagging or damage. Where the collars fit snug or tight on the assembly of the middle member and the inner member, grooves or channels can be provided along the inner member to permit fluid flow between the middle member and the inner member along the collars as described further below. Where the collars 20 do not fit tight on the assembly of middle member 18 and inner member 16 as for instrument 10, longitudinal grooves or channels 42 can be provided along an outer surface of the inner member 16 to further facilitate or assist fluid flow as shown in dotted lines in FIGS. 3 and 4.

Figure 4A:
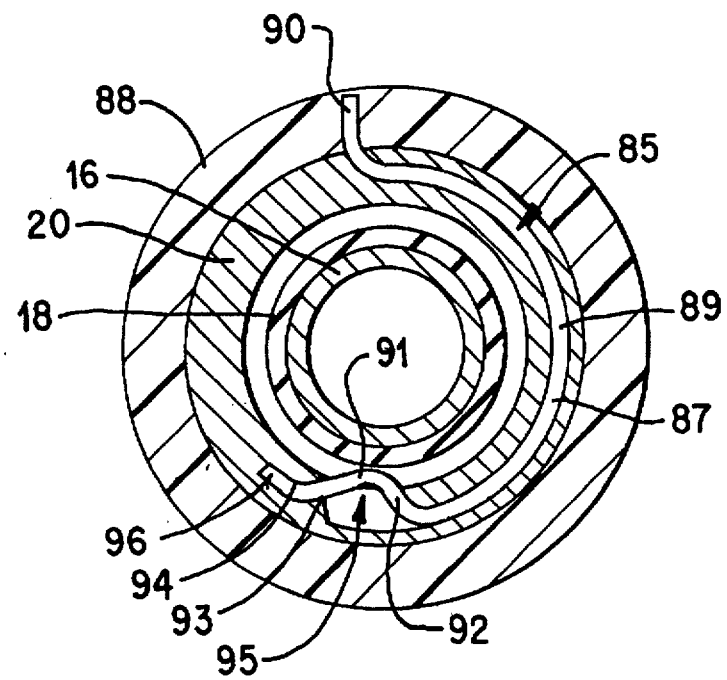
FIGS. 4A and 4B are cross-sectional views of a locking and releasing mechanism for the expandable multifunctional instruments according to the present invention.

FIGS. 4A–4F illustrate various locking and releasing mechanisms for locking the collars of the multifunctional instruments of the present invention in position on the assembly of the middle member and the inner member and for releasing the collars for movement along the assembly of the middle member and the inner member to adjust the expandable portions. FIG. 4A illustrates a locking and releasing mechanism 85 including a locking member 87 for locking collar 20 against movement on the assembly of middle member 18 and inner member 16 and an operating or releasing member 88 for releasing locking member 87 to permit movement of collar 20 along the assembly. Releasing member 88 includes a collar portion, outer member or layer such that the collar can be considered as made up of inner and outer portions, the inner collar portion corresponding to collar 20 and the outer collar portion corresponding to releasing member 88. Releasing member 88 has an annular or tubular configuration for being disposed over the length of collar 20 and is made of a resilient material, such as rubber or foam, to be squeezable or movable inwardly toward collar 20 in the direction of the instrument longitudinal axis in response to a manual squeezing or compressive force applied to releasing member 88. Locking member 87 includes a spring having a curved portion 89, an angled finger 90 at one end of curved portion 89 and a locking detent or protrusion 91 at the other end of curved portion 89. Curved portion 89 is disposed or mounted in a recess, channel or groove 96 within or on the wall of collar 20; and, as shown, the curved portion 89 is disposed in a channel 96 within and following the curvature of the collar wall. Finger 90 extends angularly or perpendicularly from the curved portion 89 and into the releasing member 88 wherein the finger 90 terminates and is secured to the releasing member 88. Detent 91 has a generally V-shaped configuration with a rearward ramp 92 angled inwardly from curved portion 89, a forward ramp 93 angled outwardly from rearward ramp 92 and a flange 94 angled from forward ramp 93 to be received in channel 96. Detent 91 protrudes through a slot 95 in the wall of collar 20 communicating with channel 96 to be normally disposed, due to the strength or bias of spring 87, in a locked portion for locking member 87 wherein detent 91 protrudes through slot 95 to be in locking engagement with the assembly of middle member 18 and inner member 16 with sufficient force to prevent movement of collar 20 thereon.

Figure 4B:
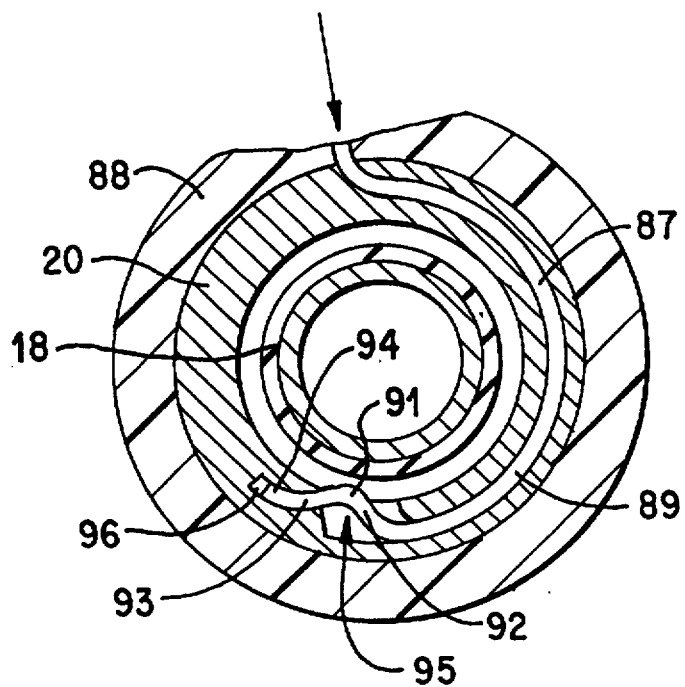

Locking member 87 is movable from the locked portion to an unlocked position wherein detent 91 is disengaged from locking engagement with the assembly of middle member 18 and inner member 16 to permit movement of collar 20 thereon by squeezing or compressing the releasing-member 88 inwardly in the direction of the instrument axis at the location of finger 90. Squeezing of releasing member 88 at finger 90 causes forward movement of spring 87 along channel 96. Forward movement of spring 87 along channel 96 causes detent 91 to move outwardly in a direction away from the instrument longitudinal axis as ramps 92 and 93 are flattened with forward ramp 93 moving forwardly further into the channel 96 as shown in FIG. 4B. Accordingly, detent 91 is moved out of locking engagement with the assembly of middle member 18 and inner member 16 such that movement of collar 20 along the assembly is permitted as long as the squeezing force on releasing member 88 is maintained. Upon removal of the squeezing force, the releasing member 88 will spring back to its normal unsqueezed or uncompressed condition carrying with it spring 87 such that detent 91 will be moved inwardly to protrude through slot 95 as the locking member 87 is returned automatically to the locked position to prevent movement of collar 20. In the locked position, detent 91 lockingly engages the assembly of middle member 18 and inner member 16 such that the collar 20 is locked in position while still permitting fluid flow between the middle member 18 and the inner member 16 through, along or past the collar 20. During use, the releasing member will be squeezed to move the locking member 87 from the normal locked position to the unlocked position to permit collar 20 to be assembled on and to be moved longitudinally and rotationally on the assembly of middle member 18 and inner member 16 and to permit collar 20 to be removed from the assembly of middle member 18 and inner member 16. Suitable indicia can be provided on releasing member 88 to identify the location of finger 90 and, therefore, the location at which the releasing member is to be squeezed.

Figure 4C:
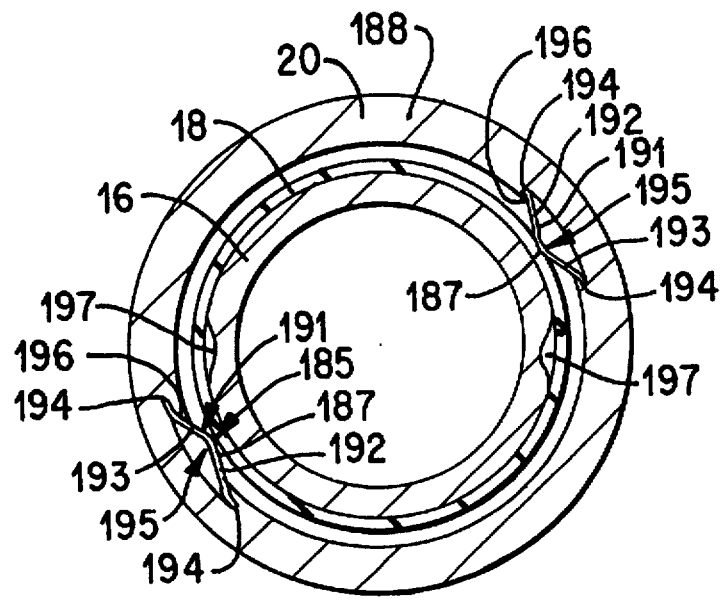
FIGS. 4C and 4D are cross-sectional views of a modification of a locking and releasing mechanism for the expandable multifunctional instruments according to the present invention.
Figure 4D:
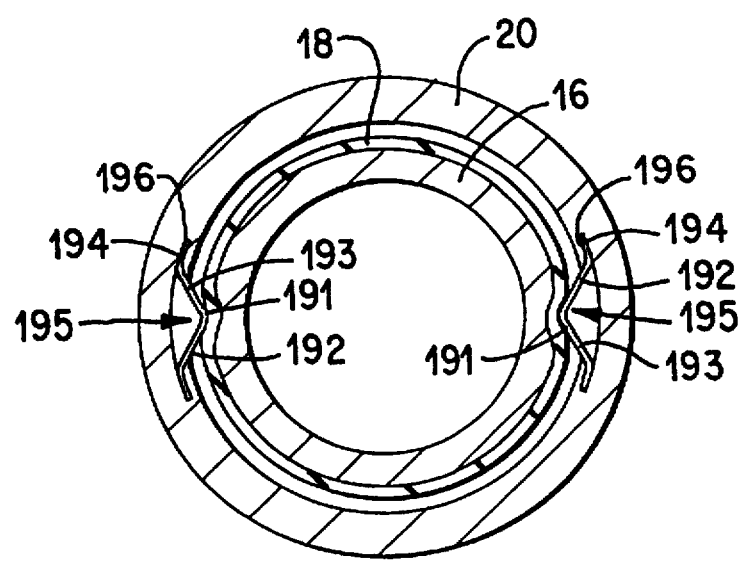

FIG. 4C illustrates at 185 a modification of a locking and releasing mechanism for use with the multifunctional instruments of the present invention. Locking and releasing mechanism 185 is similar to locking and releasing mechanism 85 except that locking member 187 of locking and releasing mechanism 185 is operated by rotation of collar 20 which serves as the releasing member 188. Locking member 187 includes at least one spring detent 191, a pair of detents 191 being shown at 180° spaced locations along collar 20. Detents 191 have generally V-shaped configurations with opposed forward and rearward ramps 192 and 193, respectively, and angled flanges 194 extending from ramps 192 and 193 to be held in channels 196 within the wall of collar 20. Detents 191 are biased in the direction of the instrument longitudinal axis to normally protrude through slots 195 in the collar 20 to be normally disposed in a locked position where the detents 191 lockingly engage the assembly of middle member 18 and inner member 16 when the collar 20 is in a first rotational position on the assembly of inner member 16 and middle member 18. In the locked position, sufficient force is exerted by detents 191 on the assembly of middle member 18 and inner member 16 to prevent longitudinal movement of collar 20 therealong while still permitting fluid flow between middle member 18 and inner member 16. Locking member 187 is movable from the locked position to an unlocked position by rotating collar 20 clockwise or counterclockwise relative to the assembly of middle member 18 and inner member 16 to a second rotational position to align detents 191 with recesses 197 extending longitudinally along an outer surface of inner member 16. The locking member 187 and the inner surface of collar 20 can be made of a slippery material to facilitate such rotation. Rotation of collar 20 to align detents 191 with recesses 197 as shown in FIG. 4D causes detents 191, due to the spring bias thereof, to be received in recesses 197, such that little or no force is applied by the detents against the assembly of middle member 18 and inner member 16, it being noted that middle member 18 is moved into recesses 197 by detents 191. With detents 191 received in recesses 197, springs 187 do not exert a locking force on the assembly of middle member 18 and inner member 16 such that longitudinal movement of collar 20 along the assembly to adjust expandable portions of the instrument is permitted. When it is desired to lock collar 20 against longitudinal movement on the assembly, collar 20 is rotated to move detents 191 out of alignment with recesses 197 causing the assembly to press against the detents such that the bias of detents 191 causes a locking force to be exerted on the assembly preventing longitudinal movement of collar 20.

Figure 4E:
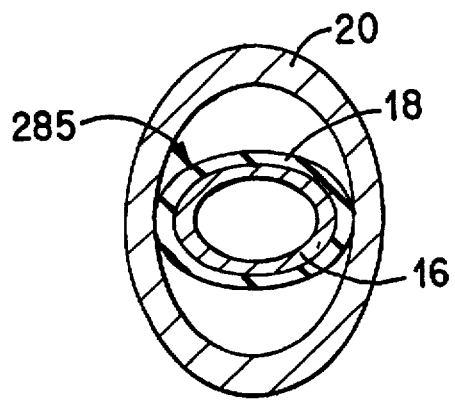
FIGS. 4E and 4F are cross-sectional views of an additional modification of a locking and releasing mechanism for the expandable multifunctional instruments according to the present invention.
Figure 4F:
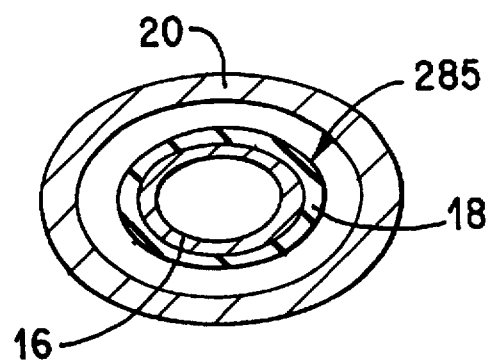

Another modification of a locking and releasing mechanism for 8 use with the instruments of the present invention is illustrated at 285 in FIG. 4E. Locking and releasing mechanism 285 is formed by configuring an inner surface of the collar and an outer surface of the assembly of the middle member and the inner member to permit longitudinal movement of the collar along the assembly of the middle member and the inner member when the collar is in a first rotational position and to prevent longitudinal movement of the collar along the assembly when the collar is rotated to a second rotational position. As shown in FIG. 4E, the outer surface or periphery of the assembly of middle member 18 and inner member 16 and the inner surface or lumen of collar 20 have non-circular configurations in cross-section with oval cross-sectional configurations being shown. The oval cross-sectional configuration of the collar inner surface has a minor dimension slightly smaller than the major dimension of the oval cross-sectional configuration for the assembly outer surface and a major dimension greater than the major dimension for the oval of the assembly outer surface. Accordingly, when the collar 20 is disposed over the assembly of middle member 18 and inner member 16 with the major dimension of the collar 20 aligned with the major dimension of the assembly in a first rotational position for the collar as shown in FIG. 4F, longitudinal movement of the collar 20 along the assembly to adjust the expandable portions is permitted. When the collar 20 is rotated 90° relative to the assembly to a second rotational position to align the minor dimension of the collar inner surface with the major dimension of the assembly outer surface, longitudinal movement of the collar 20 along the assembly will be prevented as shown in FIG. 4E. Accordingly, the collar 20 will be locked in position due to the inner surface of the collar 20 lockingly engaging the outer surface of the assembly while still allowing fluid flow between the middle member 18 and the inner member 16 along the collar 20. It should be appreciated that only the inner surface or lumen of the collar and the outer surface of the assembly need be non-circular in cross-section and that the outer surface or periphery of the collar and the lumen of the inner member can be round or circular in cross-section. In the locking and releasing mechanism of FIGS. 4E and 4F, the outer surface or periphery of inner member 16 has an oval configuration in cross-section with middle member 18 conforming to the shape of the inner member outer surface; however, the outer surface or periphery of the middle member 18 itself can have a non-circular configuration in cross-section with the inner member outer surface being circular or non-circular in cross-section.

It will be appreciated that where the collars 20 fit snug or tight upon the assembly of the middle member and the inner member as for instrument 510, the collars can be sized to contact the assembly with a friction fit sufficient to normally resist movement of the collars along the assembly while permitting movement of the collars along the assembly in response to a manual force sufficient to overcome the frictional retention of the collars on the assembly such that a separate locking and releasing mechanism may not be required.

As shown in FIG. 5, head assembly 14 is made up of a handle assembly 44, a supply system 46, a valve assembly 48 and a supplemental inlet assembly 50. Handle assembly 44 includes handle 39 mounting a proximal end of body assembly 12. Handle 39 can have any desirable configuration, including a spherical configuration as shown, to facilitate grasping by a surgeon and can be made of any suitable materials. The spherical or round configured handle 39 of instrument 10 is particularly advantageous for fitting adapters or valve entrances of other components, such as a portal sleeve housing, for universal use. A longitudinal passage 52 extends through handle 39 for receiving proximal ends of the inner member 16 and the middle member 18 and the collar 20b where the collar 20b terminates within the head assembly 14. The inner member 16 and the middle member 18 can pass entirely through the handle 39 as shown in FIG. 5 or can terminate within the handle 39. Where the collar 20b terminates within the head assembly 14, the collar 20b can pass entirely through the handle 39 or can terminate within the handle 39. Where collar 20b does not extend into the head assembly 14 as shown for instrument 10, the collar 20b can terminate adjacent handle 39. The passage 52 has a diametric or cross-sectional size to receive a proximal end of the assembly of middle member 18 and the inner member 16 with a snug fit, in which case the inner member will have grooves or channels 42, or with a loose fit to allow fluid flow between the middle member 18 and the inner member 16 along the handle 39. As shown in FIG. 5, the diameter of passage 52 is slightly greater than the outer diameter of the assembly of middle member 18 and inner member 16 to allow fluid flow between the middle member 18 and the inner member 16 along or through handle 39.

Supply system 46 for instrument 10 is formed as part of the handle assembly 44 and includes a fluid supply passage or conduit 54 extending through handle 39 and through a wall of middle member 18 to communicate with the middle member lumen 29, distally of proximal seal 31, to be coupled with expandable portions 34 by the potential or actual initial space between the middle member 18 and the inner member 16. Passage 54 terminates externally of handle 39 at a connector for connection with a source of fluid or compressible material, such as air, saline, foam or gel, to be supplied between the middle member 18 and the inner member 16 and includes a valve 56, such as a stop cock, for controlling fluid flow therethrough. Accordingly, fluid supplied to middle member lumen 29 via fluid supply system 46 will cause expansion or distension of middle member 18 from the non-expanded position toward an expanded or distended position or condition, and release of fluid from lumen 29 will cause movement of middle member 18 from the expanded position toward the non-expanded position. It will be appreciated that the expandable portions 34 can be moved between the expanded and non-expanded positions in many various ways including fluidically or hydraulically as exemplified by instrument 10, fluidically via absorption of fluids, such as body fluids, as exemplified by instrument 1010 and mechanically with the use of a mechanical device such as a support or spine, as disclosed in applicant's U.S. Pat. No. 5,074,840 and Ser. No. 07/600, 775 filed Oct. 23, 1990, the disclosures of which are incorporated herein by reference. A second supply conduit or passage 58 terminating externally of handle 39 at a connector and including a valve 60, such as a stopcock, extends through handle 39 and through the walls of the middle member 18 and the inner member 16 to communicate with the inner member lumen 25 for introducing fluids, such as insufflation gas, instruments and medicaments, for example, in the anatomical cavity or for aspirating fluids and materials from the anatomical cavity via the lumen of the inner member and the passage 58. Valves 56 and 60 can be arranged on head assembly 14 in many various ways; however, the bilateral arrangement illustrated for instrument 10 is particularly advantageous for ease of use. The number of inlet valves provided can vary; however, it is preferred that at least two stopcocks be provided on handle 39 to facilitate and expand the areas of procedural use and to assist in preventing leakage through head assembly 14 as explained further below.

Figure 6:
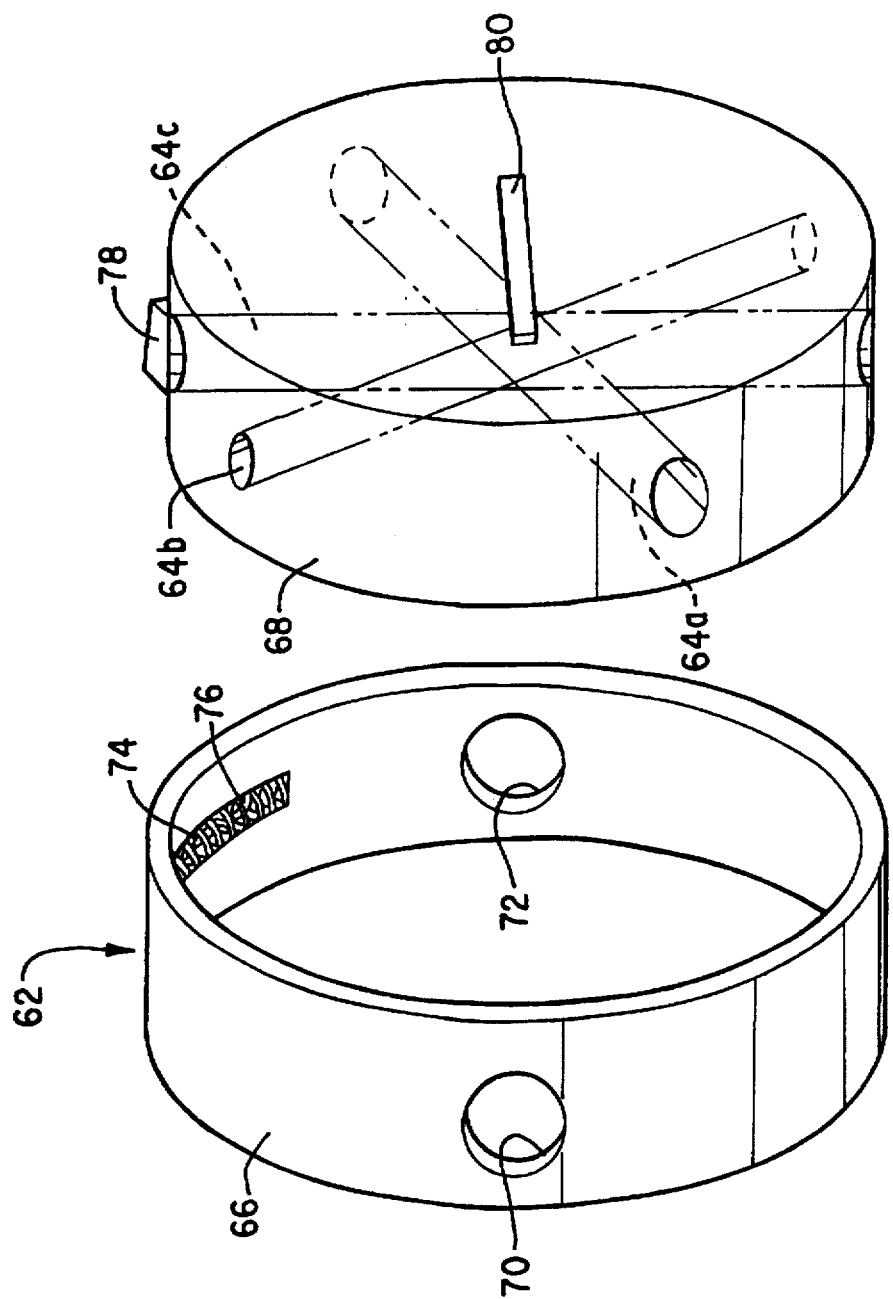
FIG. 6 is an exploded perspective view of the valve assembly for the head assembly of FIG. 5.
Figure 7:
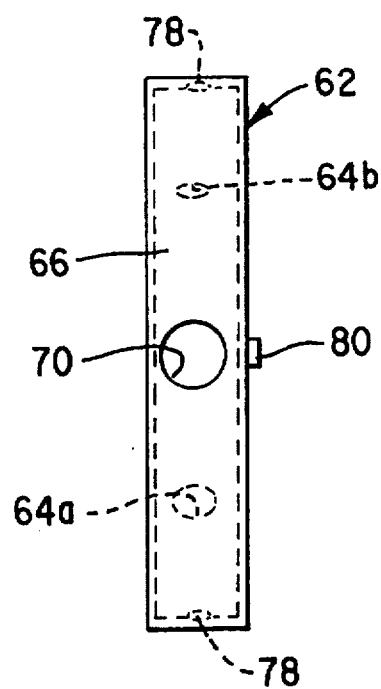
FIG. 7 is a front plan view of the valve assembly of FIG. 6.
Figure 8:
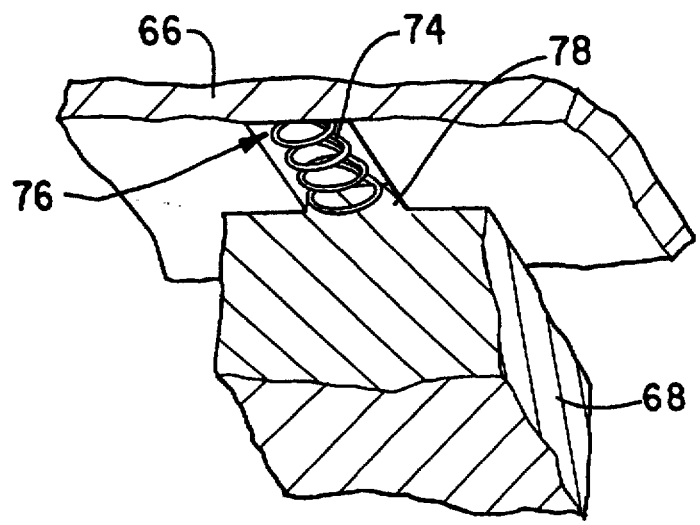
FIG. 8 is a broken perspective view, partly in section, of the valve assembly of FIG. 6.

Valve assembly 48 includes a valve 62 for allowing instruments to be inserted in the inner member lumen 25 and for closing off or sealing the lumen 25 when no instrument passes through the valve assembly 48. Valve 62 is shown as an adjustable valve having a plurality of different sized valve passages 64 selectively alignable with lumen 25; however, any other suitable valve construction can be provided. As shown in FIGS. 6 and 7, valve 62 includes an annular valve head 66 and a flat, circular valve body 68 of substantially uniform thickness rotatably disposed in valve head 66. Longitudinally aligned, opposed forward and rearward openings 70 and 72, respectively, are formed in the valve head 66 and are aligned with inner member lumen 25. A plurality of diametric, intersecting valve passages 64a, 64b and 64c of different diameters are formed in the valve body 68 for being selectively aligned with openings 70 and 72. The valve body 68 is biased to a position of non-alignment with valve head 66 wherein the valve passages 64a, 64b and 64c are not aligned with the openings 70 and 72 such that the lumen 25 is closed off or sealed when no instrument or object passes through the valve assembly 48 as shown in FIG. 5. The valve body 68 can be biased to the position of non-alignment in many various ways including the use of one or more bias devices 74, such as a helical coil spring 74. Spring 74 is disposed in a recess or groove 76 extending in a circumferential direction along an inner surface of the valve head 66. A protrusion including a shoulder or ridge 78 extends outwardly from an outer circumferential wall of the valve body 68 to be received in the recess 76 as shown in FIG. 8. Spring 74 is mounted in compression between a forward wall of recess 76 and the protrusion 78 to rotationally bias the valve body 68 relative to the valve head 66, in a clockwise direction looking at FIGS. 5 and 6, to the position of non-alignment wherein protrusion 78 is biased against a rearward wall of recess 76 and valve passages 64a, 64b and 64c are not aligned with openings 70 and 72.

A knob 80 is provided along a side wall of the valve body 68 for manually rotating the valve body 68, i.e. counterclockwise looking at FIGS. 5 and 6, relative to the valve head 66 against the bias of spring 74 to selectively align one of the valve passages 64a, 64b or 64c with the openings 70 and 72. With one of the valve passages 64a, 64b or 64c aligned with the openings 70 and 72, instruments can be introduced through the inner member lumen 25 via the aligned passage and openings of the valve assembly 48. When no instrument passes through the valve assembly 48, the rotational bias of spring 74 in the clockwise direction causes the valve body 68 to be automatically moved to the position of non-alignment with the valve head 66. Predisposed non-alignment of the valve passages 64a, 64b and 64c with the openings 70 and 72 is desirable in that escape or leakage through the valve assembly 48 of fluid, such as insufflation gas including air or carbon dioxide, supplied to an anatomical cavity in the course of many surgical and diagnostic procedures to facilitate visualization, enhance access and increase space, for example, is prevented or minimized. Recess 76 can have a length selected in accordance with the amount of rotation required of the valve body 68 relative to the valve head 66 to selectively align the valve passages 64a, 64b and 64c with the than one protrusion 78 can be provided in valve assembly 48 for being biased by more than one bias device. Valve assembly 48 can be permanently or removably mounted to the handle assembly 44 in many various ways, and the valve assembly 48 can be disposed distally of or proximally of the handle assembly 44. As shown in FIG. 5, valve assembly 48 is mounted to handle assembly 44 by a tubular neck 45 extending distally from an outer wall of valve head 66 to join handle 39.

A proximal end of the body assembly 12 is mounted to the head assembly 14 with the inner member lumen 25 aligned with valve openings 70 and 72; and, as shown in FIG. 5, proximal end 28 of middle member 18 and proximal end 24 of inner member 16 extend through the neck to be secured to the outer wall of the valve head 66 such that the valve head outer wall forms proximal seal 31. Accordingly, the potential space between the middle member 18 and the inner member 16 is sealed both proximally and distally allowing the middle member 18 to be expanded or distended by fluid supplied between middle member 18 and inner member 16 via passage 54. Depending on the location and structure of proximal seal 31, the body assembly 12 can be permanently or removably mounted to the head assembly 14. The body assembly 12 can be removably mounted to the head assembly 14 in many various ways, such as adhesively, frictionally or mechanically with the use of threads or other detent mechanisms, and the body assembly 12 can be permanently or removably mounted to any part of the head assembly 14.

Supplemental inlet assembly 50 includes a tube or conduit 82 extending proximally from the valve assembly 48, the tube 82 having a lumen aligned with valve opening 72 and a valve 84 for selectively closing and opening the supplemental inlet lumen. Although valve 84 need not be provided, it is desirable that at least three inlet valves 60, 62 and 84 be provided to ensure no leakage through the head assembly 14 when instruments are inserted and removed and throughout the entire medical procedure being performed. For example, when valve 84 is opened, such as to insert and/or withdraw instruments, no leakage through head assembly 14 will occur due to valves 60 and 62 being closed. Accordingly, leakage of gas, such as insufflation gas, utilized during the medical procedure can be prevented. The supplemental inlet lumen can have a substantially uniform diameter along the length thereof, or the supplemental inlet lumen can have a gradually increasing diameter in a proximal direction to facilitate insertion of instruments therethrough.

In use, the multifunctional instrument 10 can be provided with collars 20 assembled on the assembly of middle member 18 and inner member 16 or without collars 20 already assembled thereon in which case the collars 20 are placed on the assembly of middle member 18 and inner member 16 prior to use such as by sliding the collars over the middle member distal end 26. It should be appreciated, however, that the collars can be assembled on the assembly of the middle member and the inner member in many various ways in accordance with the structure of the collars. For example, where the collars are formed with spaces or slots communicating with the collar lumens, such as for C-shaped or U-shaped collars, the collars can be snapped or clipped onto the assembly of the middle member and the inner member, and the collars can be made of a flexible material to facilitate assembly of the collars on the assembly of the middle member and the inner member with a snap fit. Once the collars 20 are assembled on the assembly of middle member 18 and inner member 16, the collars 20 can be moved or slid longitudinally along the middle member 18 to define expandable portions 34 having a desired length, position and separation distance. By providing a plurality of collars 20 of different lengths, a desired number of expandable portions 34 can be obtained having desired lengths, positions and separation distances in accordance with the procedure to be performed.

Figure 9:
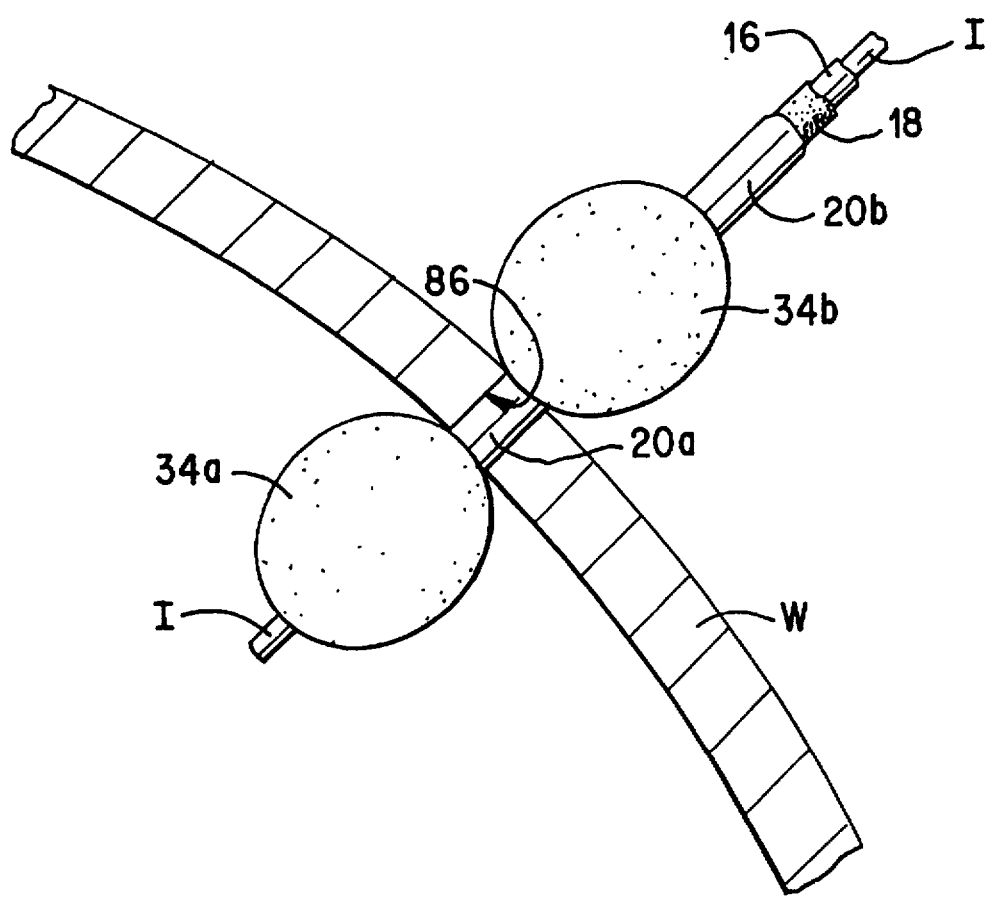
FIG. 9 is a broken side view, partly in section, of the expandable multifunctional instrument of FIG. 1 during use with the expandable portions of the instrument in an expanded position.

Once the collars 20 are positioned as desired on the assembly of middle member 18 and inner member 16, a distal end of the body assembly 12 is introduced in an anatomical cavity through a relatively small size natural or artificial anatomical opening 86, as shown in FIG. 9, in a wall W of the anatomical cavity with the expandable portions 34a and 34b in the non-expanded position of FIG. 1. The instrument 10 can be in the nature of a portal sleeve providing a passage through the anatomical cavity wall, or the instrument 10 can be introduced in the anatomical cavity via a portal sleeve depending on procedural use. In the non-expanded position, expandable portion 34a has a cross-sectional size substantially the same as or smaller than the cross-sectional size of collar 20a to facilitate introduction through anatomical opening 86. Where the collar 20a is to extend through the opening 86 during use, the cross-sectional size of collar 20a is selected to correspond substantially to the cross-sectional size of the anatomical opening 86, and the length of collar 20a is selected to correspond substantially to the thickness of wall W as shown in FIG. 9. Expandable portion 34a is positioned in the anatomical cavity, and expandable portion 34b is positioned externally of the anatomical cavity with collar 20a disposed in anatomical opening 86 to extend along the thickness of the cavity wall W. Once the expandable portions 34a and 34b have been properly positioned on each side of the anatomical cavity wall W, fluid, which can be an antiseptic fluid, is supplied between the inner member 16 and the middle member 18 via fluid supply passage 54 to expand, distend or inflate the middle member 18 and thusly move the expandable portions 34a and 34b in a direction radially outwardly of the instrument longitudinal axis from the non-expanded position to the expanded position shown in FIG. 9, with expansion or distension of the middle member 18 being constrained along the non-distensible portions defined by collars 20. The size of expandable portions 34a and 34b in the expanded position can be controlled by controlling the flow of fluid between the middle and inner members via valve 56 such that the size of the expandable portions in the expanded position can be made larger or smaller. Additionally, by controlling the quantity of material within the expandable portions, the expandable portions can be made more or less compliant and soft to conform to the contour of anatomical cavity or firm and rigid while still being able to flex or "give".

In the expanded position, which can be maintained by closing valve 56, expandable portions 34a and 34b form enlargements or protuberances having a cross-sectional size larger than the cross-sectional size of the expandable portions in the non-expanded position. As shown in FIG. 9, the expandable portions 34a and 34b have a predetermined round or toroidal configuration and are disposed adjacent internal and external surfaces, respectively, of the cavity wall W. Expandable portions 34a and 34b close off or seal the anatomical opening 86 and anchor or stabilize the instrument 10 relative to the cavity wall W. The instrument 10 can be used to gently manipulate tissue within or forming the anatomical cavity such as by lifting, pushing, exposing, separating or dissecting tissue or organ structure within or forming the anatomical cavity with expandable portions 34, and the instrument 10 can be used to create a space or increase the size of a space in the anatomical cavity to improve access or visualization. Where the inner member 16 has a lumen or passage therein, various other instruments I, such as an endoscope or instruments for performing electrosurgical or laser procedures, can be introduced at the anatomical cavity via supplemental inlet assembly 50, valve assembly 48 and the lumen 25 of the inner member 16. If desired, the distal end of body assembly 12 can be coupled with a source of light for illuminating a site in the anatomical cavity. For example, inner member 16 can contain one or more light transmitting fibers for transmitting light from a light source, such as a bulb in head assembly 14, to the distal end of the body assembly 12. Fluids and other substances can be introduced at or aspirated from the anatomical cavity via the supplemental inlet assembly 50 or via supply passage 58. Instruments can also be introduced at the anatomical cavity via supply passages 54 and 58. It should be appreciated that various instruments can be introduced at the anatomical cavity via the multifunctional instrument 10 and that where electrosurgical and/or laser instruments are introduced, various electrosurgical and laser procedures such as cautery, coagulation and/or cutting, can be performed. Additionally, head assembly 14 can be provided with a terminal for connection with a source of electrical energy to allow treatment of tissue with electrical energy via the middle member 18 where the middle member is made of electrically conductive material or includes electrically conductive material, fibers, a spine or reinforcement within or on the middle member. When it is desired to withdraw the instrument 10 from the anatomical cavity, fluid can be removed from the middle member 18 via the valve assembly 46 causing movement of expandable portions 34 to the non-expanded position facilitating withdrawal from the body via the narrow opening. Alternatively, the middle member 18 can be punctured or burst, such as with a sharp implement inserted through the instrument 10 or in the anatomical cavity to burst one or more of the expandable portions 34, allowing the fluid to be released in the body as is desirable when the fluid supplied between the inner member 16 and the middle member 18 is an antiseptic fluid.

One or more collars 20 can be provided in the multifunctional instrument 10 for adjustability at the point of use and in accordance with the number of expandable portions 34 desired depending on procedural use. Where the middle member 18 is resilient, the size of the expandable portions 34 in the expanded condition can be controlled by controlling flow of material or fluid between the middle member 18 and the inner member 16. The size of the expandable portions in the expanded position can be controlled by adjusting the length of the expandable portions 34 in that, for example, the size of the expandable portions 34 in the expanded condition can be made smaller by moving the collars 20 closer together and can be made larger by moving the collars 20 farther apart. The collars 20 can have various configurations or structure to control the shape and/or size of the expandable portions 34 in the expanded condition. Additionally, the expandable portions 34 themselves can be formed to control the shape and/or size of the expandable portions in the expanded condition. For example, the middle member 18 can have various preformed shapes or can be formed with segments or portions thereof of different densities or elasticities such that some segments are more resistant to expansion or inflation than other segments to obtain various predetermined configurations for the expandable portions in the expanded condition and/or to obtain different sizes for the individual expandable portions. The expandable portions can have various predetermined configurations or shapes in the expanded condition such as spherical, toroidal, triangular, multi-lobed, pear-shaped, spoon shaped, fan shaped, dumbbell shaped and onion-shaped configurations.

The handle assembly 44, supply system 46, valve assembly 48 and supplemental inlet assembly 50 can be formed integrally, unitarily or as separate components removably or permanently attached to one another. The body assembly 12 can be formed integrally, unitarily with the head assembly 14 or can be removably mounted thereto. The handle assembly 44 can be disposed distally of the valve assembly 48 as shown or proximally thereof, and the head assembly 14 can be provided with or without the supplemental inlet assembly 50. Handle assembly 44 can have a configuration to resist insertion of the instrument 10 into an anatomical cavity beyond a predetermined distance, and the handle 39 can have a configuration corresponding to the configuration of an anatomical organ structure. The diameters of the valve passages 64 are preferably selected to correspond substantially to the external sizes or diameters of instruments to be inserted therethrough so as to provide lateral support for the inserted instruments and to minimize any gap or space between the inserted instruments and the valve assembly 48 to prevent leakage of fluid.

Figure 9A:
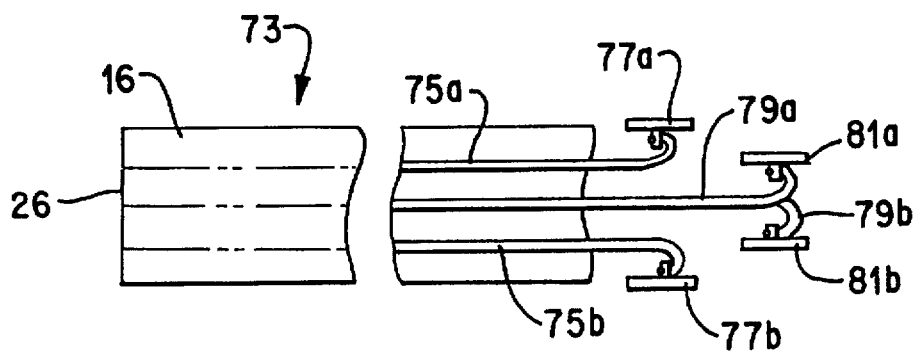
FIG. 9A is a broken, top plan view of an adjustment system for the expandable multifunctional instruments according to the present invention.
Figure 9B:
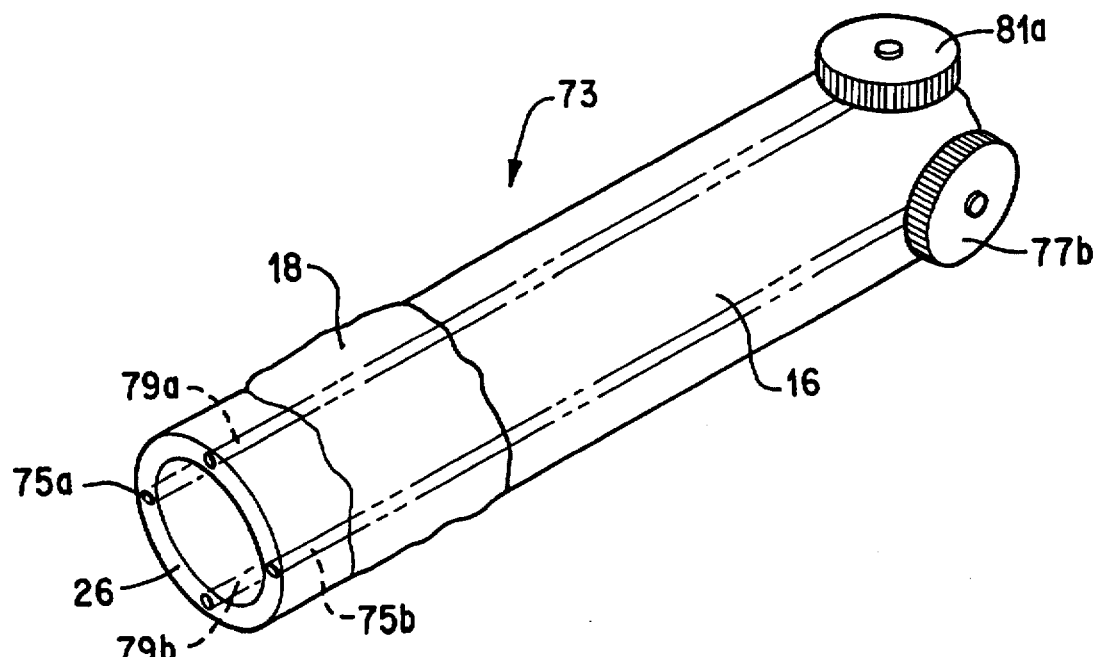
FIG. 9B is a broken perspective view of the adjustment system of FIG. 9A.

FIGS. 9A and 9B illustrate at 73 a system for adjusting or changing the orientation or direction of the body assembly during use where the inner member is made of flexible or bendable material. As shown in FIGS. 9A and 9B, left and right control wires 75A and 75B are disposed within the wall forming inner member 16 or within recesses along an outer surface of the inner member 16. Wires 75A and 75B are disposed on opposing lateral sides of inner member 16 and extend longitudinally therealong. Wires 75A and 75B have distal ends connected with inner member distal end 26 and proximal ends connected with left and right control wheels 77A and 77B, respectively, mounted on or to head assembly 14 (not shown). Upper and lower control wires 79A and 79B are disposed within the wall forming inner member 16 or within recesses along an outer surface of the inner member 16 at opposing upper and lower sides, respectively, of inner member 16. Wires 79A and 79B extend longitudinally along the inner member 16 and have distal ends connected with inner member distal end 26 and proximal ends connected with upper and lower control wheels 81A and 81B, respectively, mounted on or to head assembly 14. Wires 75 and 79 are movable proximally and distally in response to winding or rotation in a first direction of wheels 77 and 81 and in response to unwinding or rotation in a second direction of wheels 77 and 81, respectively, such that the wires 75 and 79 are wound or shortened, and unwound or lengthened around pins or axles of the control wheels. Movement of one or more wires 75 and 79 by the control wheels results in a corresponding force being applied to inner member 16 due to connection of the wires with the inner member distal end 26. Accordingly, winding or pulling of left control wire 75A in the proximal direction by left control wheel 77A will cause the distal end 26 of inner member 16 to move to the left, looking proximally at FIG. 9B, and pulling of right control wire 75B by right control wheel 77B will cause the inner member distal end 26 to move to the right. Similarly, pulling of upper and lower control wires 79A and 79B in the proximal direction by upper and lower control wheels 81A and 81B, respectively, will cause the inner member distal end 26 to move up and down, respectively, as shown in dotted lines in FIG. 1. It will be appreciated that various combinations of movements can be used to adjust the orientation of distal end 26 and that the collars 20 can be flexible or bendable to be moved by the inner member 16. Distal movement of the control wires via unwinding by the control wheels will result in reverse movements of the inner member to straighten the inner member longitudinally. The control wheels can be provided with various mechanisms, such as releasable ratchet mechanisms, for locking the position of the control wheels to maintain the adjusted position for inner member 16. It should also be appreciated that the control wires can be manipulated in various ways in addition to the control wheels and that the right and left directional adjustments can be provided with a single control wheel and the up and down directional adjustments can be provided with a single control wheel.

Where the adjustment system is provided in the multifunctional instruments of the present invention, use is similar to that previously described except that the angular orientation, direction or position of the body assembly distal end can be changed or adjusted subsequent to introduction in the anatomical cavity via operation of control wheels 77 and 81 to move wires 75 and 79 and, therefore, the distal end of the body assembly with the middle member 18 moving with the inner member 16. FIG. 1 shows in dotted lines the distal end of body assembly 12 moved upwardly substantially 180° from its initial position.

Figure 10:
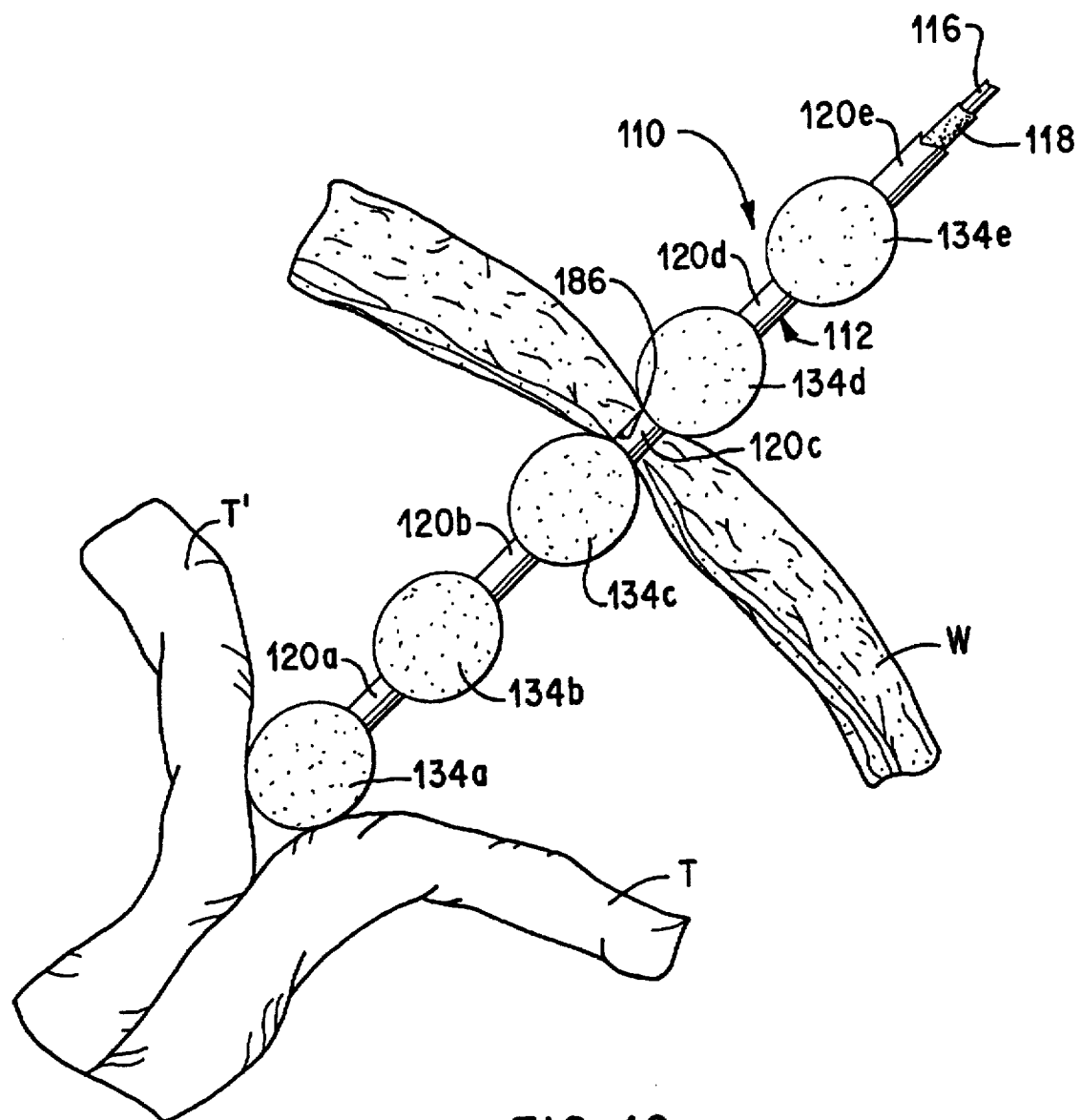
FIG. 10 is a broken side view, partly in section, of a modification of an expandable multifunctional instrument according to the present invention during use with the expandable portions of the instrument in an expanded position.

A modification of a multifunctional instrument according to the present invention is illustrated in FIG. 10 at 110 wherein only the body assembly 112 for instrument 110 is shown. Instrument 110 is similar to instrument 10 except that five collars 120a, 120b, 120c, 120d and 120e are provided along the assembly of middle member 118 and inner member 116 at spaced locations to define five expandable portions 134a, 134b, 134c, 134d and 134e.

Utilization of multifunctional instrument 110 is similar to that described above for instrument 10 in that a distal end of the body assembly 112 is introduced through a natural or artificial opening 186 in a tissue or organ structure, such as anatomical cavity wall W, with the expandable portions 134 in the non-expanded position. Expandable portions 134a, 134b and 134c are positioned on one side of anatomical wall W to be disposed within the anatomical cavity, and expandable portions 134d and 134e are positioned on an opposite side of wall W to be disposed externally of the anatomical cavity with collar 120c disposed in anatomical opening 186. Once the expandable portions 134 have been properly positioned, fluid is supplied between the middle member 118 and the inner member 116 to move the middle member 118 outwardly in a radial or transverse direction to the expanded condition illustrated in FIG. 10. Instrument 110 is particularly useful for separating adhering tissue (lysis of adhesion) in that expandable portion 134a can be utilized to gently separate tissue or organ structure T from tissue or organ structure T' as may be necessary in many various procedures, such as various exploratory procedures where the presence of bodily fluids may have caused undesirable adhering of tissues T and T'. By providing a plurality of expandable portions 134, the instrument 110 facilitates procedural use where more than one expanded portion is needed to fill a cavity, to fit within a cul de sac or to fit between organ structures.

Another modification of a multifunctional instrument in accordance with the present invention is illustrated in FIG. 11 at 210, only the body assembly 212 for instrument 210 being shown. Multifunctional instrument 210 is similar to multifunctional instrument 10 except that forward and rearward edges 236 and 238, respectively, for collar 220 of instrument 210 are inwardly curving. Forward edge 236 has diametrically opposed edge segments 247, only one of which is shown, curving inwardly from a plane containing diametrically opposed, distal most edge segments 249, such plane being disposed transverse or perpendicular to a longitudinal axis of collar 220. Similarly, rearward edge 238 has diametrically opposed edge segments 247' curving inwardly from a plane containing diametrically opposed, proximal most edge segments 249', such plane being disposed parallel with the plane of the distal most edge segments 249. Curved, concave edge segments 247 and 247' are particularly advantageous for shaping the expandable portions 234a and 234b upon expansion thereof so that the expandable portions 234 in the expanded condition extend partially back over the collar 220 due to the curvature of the edge segments 247 and 247' to form a round or spherical configuration particularly useful in vascular procedures, such as for blocking or occluding blood vessels.

Figure 12:
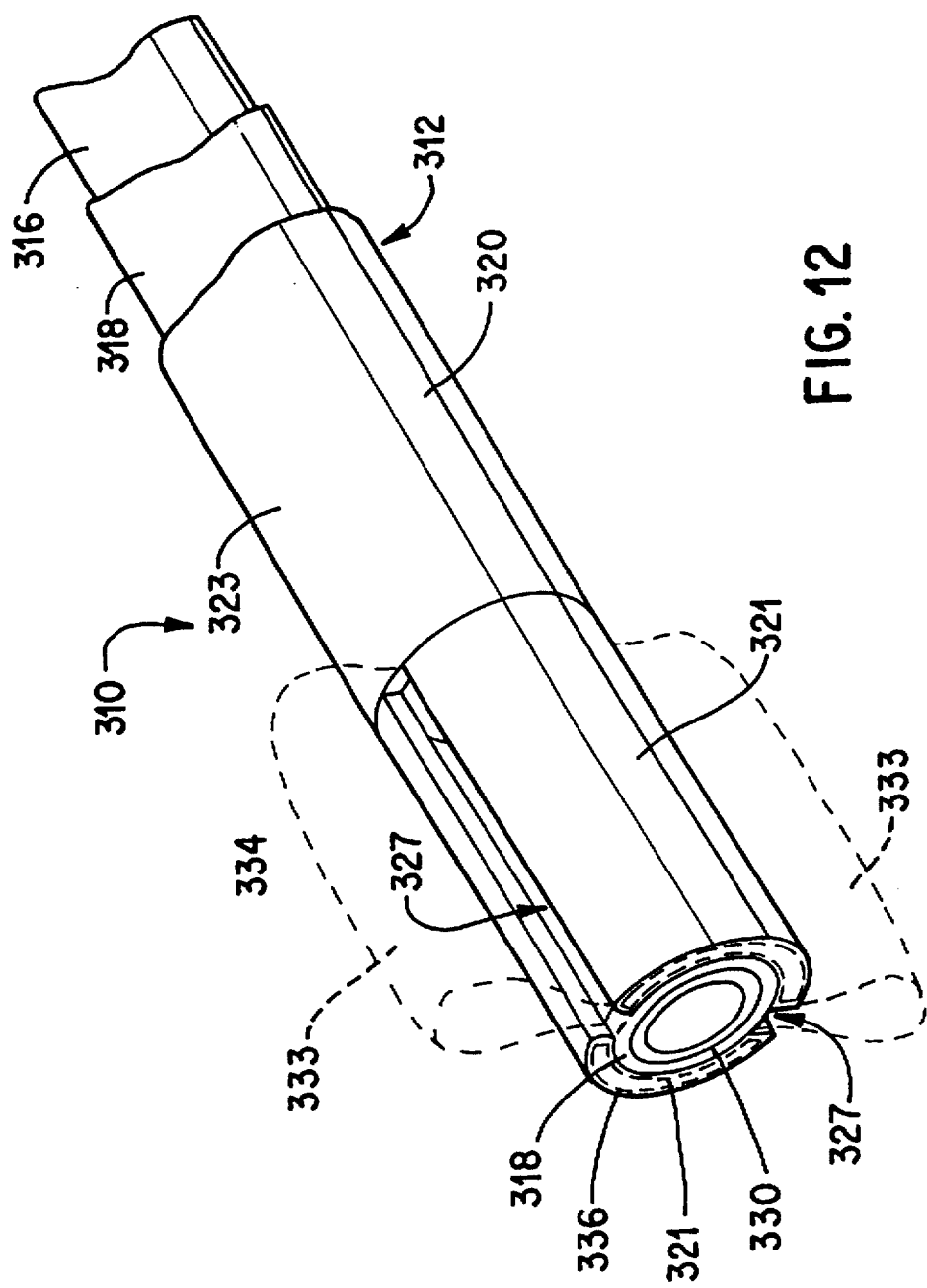
FIG. 12 is a broken perspective view of another modification of an expandable multifunctional instrument according to the present invention.

Another modification of a multifunctional instrument according to the present invention is illustrated in FIG. 12 at 310, only the body assembly 312 for multifunctional instrument 310 being shown. Multifunctional instrument 310 is similar to multifunctional instrument 10 except that collar 320 for multifunctional instrument 310 includes one or more spaced legs 321 extending longitudinally from a tubular body 323 of the collar 320 parallel or in alignment with a longitudinal axis of the instrument 310. Two legs 321 are shown in FIG. 12 separated from one another by longitudinally extending gaps or spaces 327 through which middle member 318 extends when moved from the non-expanded condition to the expanded condition. Distal seal 330 is aligned with forward edge 336 of collar 320, i.e. the forward edges 336 of legs 321; and, when fluid is supplied between middle member 318 and inner member 316, expandable portion 334 is moved outwardly through the spaces 327. Accordingly, expandable portion 334 in the expanded condition forms a plurality of spaced lobes 333, shown in dotted lines, extending in a direction radially outwardly of the longitudinal axis of the multifunctional instrument 310. Spaces 327 are disposed at 180° spaced locations about the longitudinal axis of instrument 310; however, spaces 327 can be arranged about the longitudinal axis of the instrument 310 in many various ways in accordance with the arrangement or spacing desired for the lobes 333. It will be appreciated that by varying the size and number of the spaces 327, a desired number of lobes 333 of desired size can be obtained for the expandable portion 334 in the expanded condition.

Figure 13:
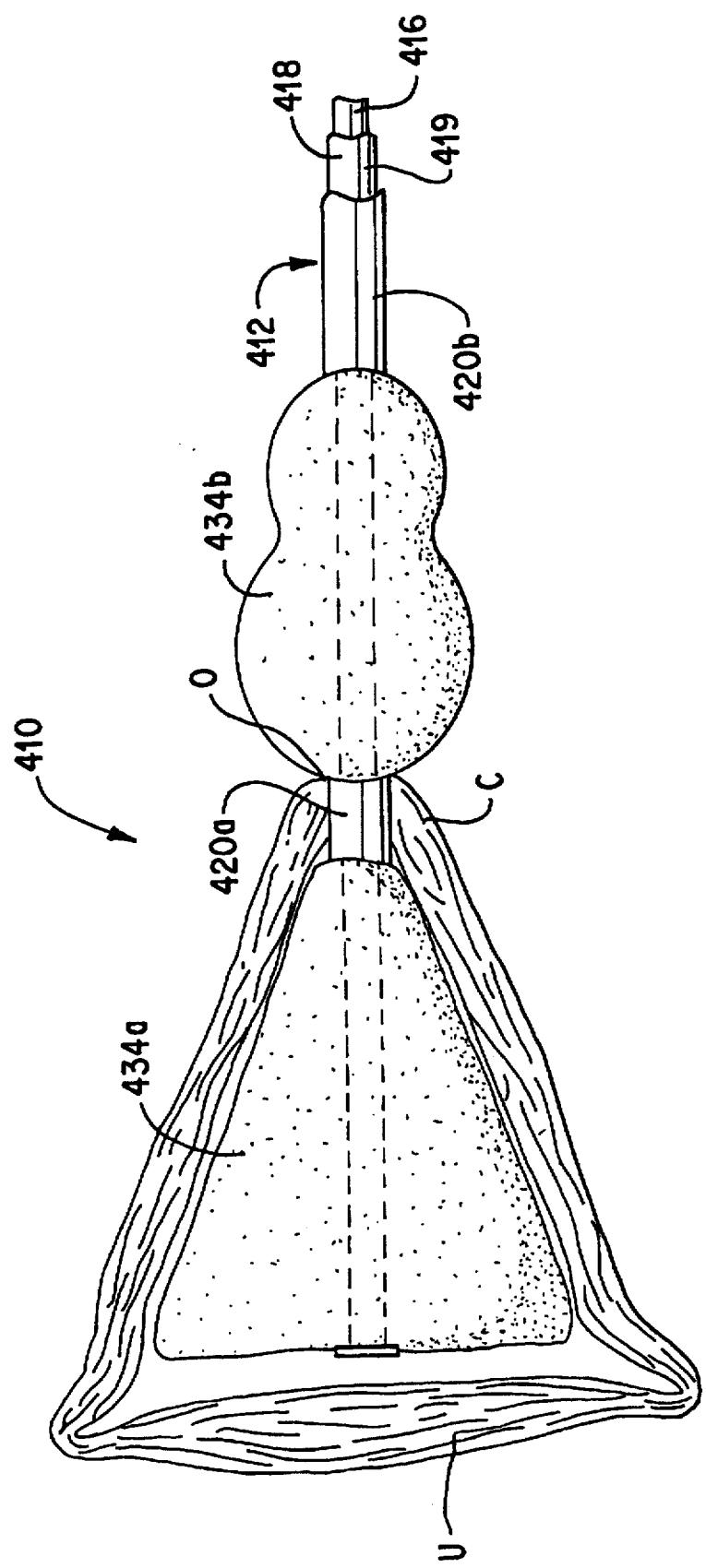
FIG. 13 is a broken side view of a further modification of an expandable multifunctional instrument according to the present invention.

A further modification of a multifunctional instrument according to the present invention is illustrated in FIG. 13 at 410, only the body assembly 412 for the instrument 410 being shown. Multifunctional instrument 410 is similar to multifunctional instrument 10 except that middle member 418 of instrument 410 is made of a non-elastic, non-stretchable, rigid material defining expandable portions 434 having a preformed predetermined shape. Multifunctional instrument 410 includes expandable portions 434a and 434b separated by a collar 420a with a collar 420b disposed proximally of expandable portion 434b, the collars 420a and 420b being similar to collars 20. Middle member 418 along expandable portion 434a has a preformed triangular or conical configuration particularly useful for uterine use and along expandable portion 434b has a preformed pear-shaped configuration. The middle member 418 is made as a collapsible bag, balloon or membrane of elastic or plastic material shaped to have the desired performed configurations along expandable portions 434a and 434b, and has connecting portions 419, which can be tubular, connecting expandable portions 434 and disposed within collars 420. The middle member 418 can be folded, rolled, crumpled or collapsed in the non-expanded position to facilitate introduction through a relatively small size anatomical opening.

Use of multifunctional instrument 410 is similar to that previously described in that one or both of the expandable portions 434 are introduced through an opening in tissue or organ structure of the body in the non-expanded or collapsed position. As shown in FIG. 13, the expandable portion 434a is introduced in the uterus U through the cervix C to position expandable portion 434b adjacent the external cervical os O with the collar 420a extending along the cervix. Once the expandable portions 434 are properly positioned in accordance with the procedure to be performed, fluid is supplied between middle member 418 and inner member 416 to move the expandable portions 434 from the collapsed position to the expanded position wherein the expandable portions 434 form enlargements or protrusions having configurations corresponding to the preformed predetermined shapes. The triangular shape of expandable portion 434a in the expanded position is particularly advantageous for uterine use, such as uterine manipulation, and the pear-shaped configuration of expandable portion 434b closes off or seals the external cervical os O. In the expanded position, the enlargements defined by expandable portions 434a and 434b internally and externally of the cervix C serve to stabilize the instrument 410 during use. Depending on procedural use, expandable portion 434a can have an external size in the expanded position to fill the uterus U and contact the internal uterine wall. Where the middle member 418 includes electrically conductive material within or forming the middle member, such as an electrically conducting spine, the instrument 410 can be used for electrical coagulation or cautery, such as to perform uterine ablation. Various spines useful in the present invention are disclosed in applicant's prior application Ser. No. 07/600,775, filed Oct. 23, 1990, the disclosure of which is incorporated herein by reference.

Figure 14:
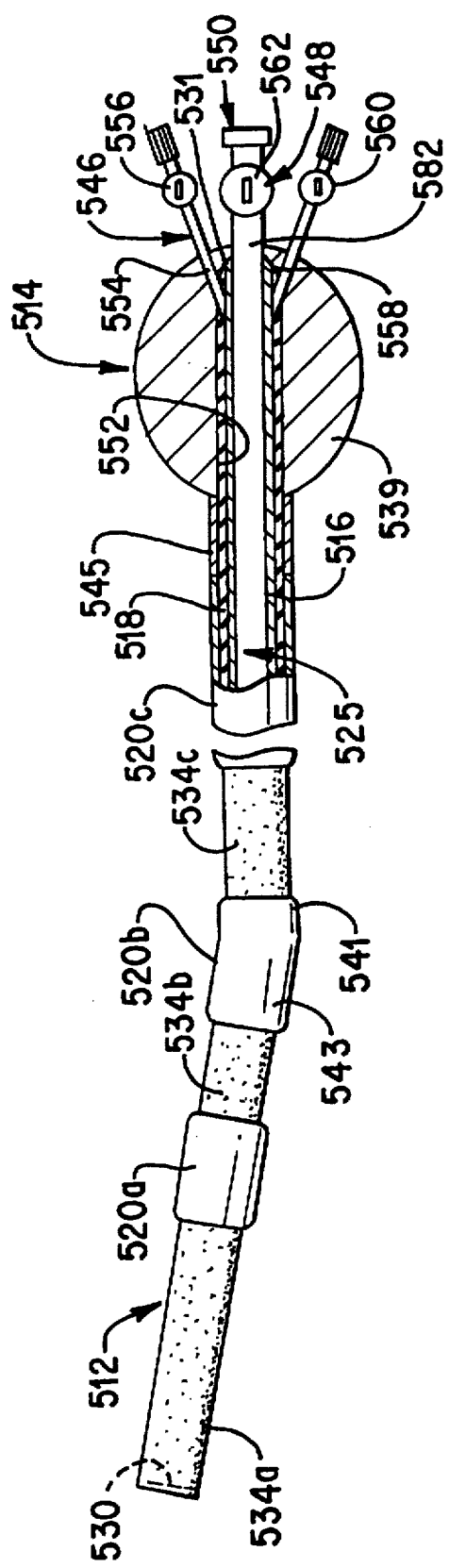
FIG. 14 is a broken side view, partly in section, of yet another modification of an expandable multifunctional instrument of the present invention.

An additional modification of a multifunctional instrument according to the present invention is illustrated at 510 in FIG. 14. Body assembly 512 for multifunctional instrument 510 includes inner member 516, middle member 518 receiving inner member 516 and collars 520a, 520b and 520c disposed on the assembly of middle member 518 and inner member 516. As shown in FIG. 15, inner member 516 is similar to inner member 16 except that inner member 516 is angled or bent to have a non-straight configuration and includes one or more longitudinally extending grooves or channels 542, two channels 542 being shown. Inner member 516 has a proximal section 535 aligned with a longitudinal axis of instrument 510 and a distal section 537 disposed at an angle with the proximal section 535 and with the instrument longitudinal axis. Grooves or channels 542 are formed along an outer surface of the inner member 516 and can extend the entire or less than the entire length of inner member 516 in accordance with the location of expandable portions 534, two channels 542 being shown in FIG. 15. The channels 542 can be of the same or different lengths and can be arranged on the inner member in many ways, the channels 542 being arranged at 180° spaced locations.

Figure 17:
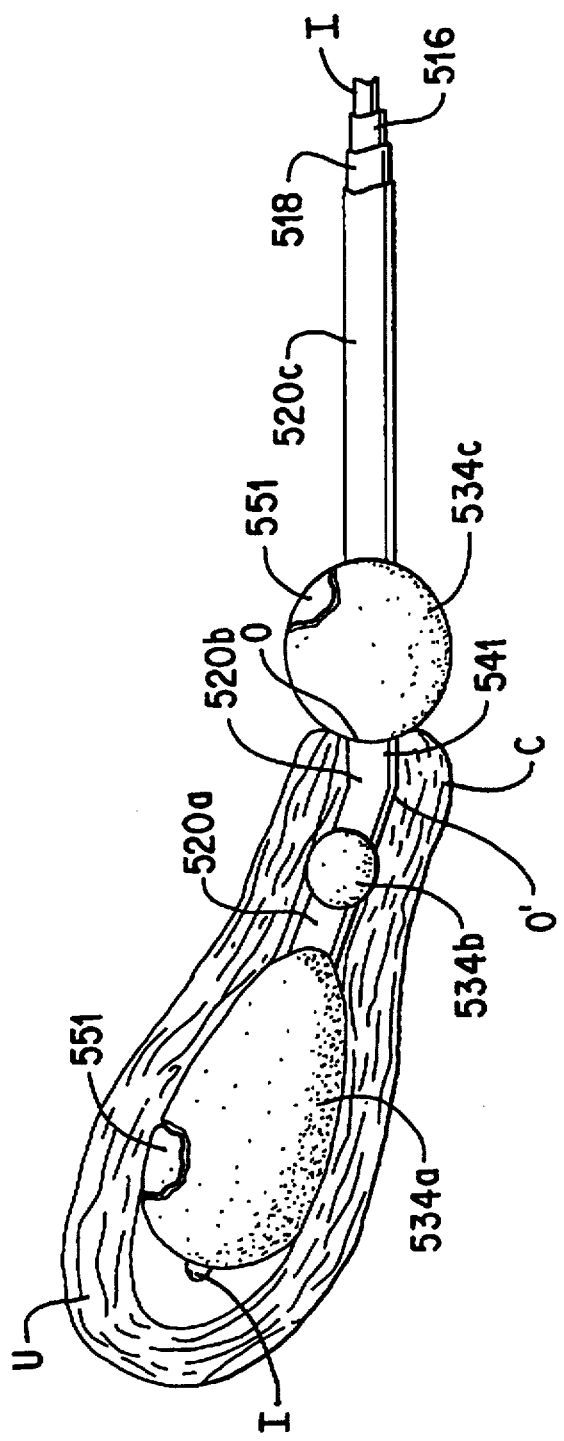
FIG. 17 is a broken side view, partly in section, of the expandable multifunctional instrument of FIG. 14 during use with the expandable portions in the expanded position.

Middle member 518 is similar to middle member 18 and is in the nature of a tubular balloon for being assembled over inner member 516 with a tight fit or with a loose fit, the middle member 518 being assembled over the inner member 516 with a tight fit as shown in FIG. 16 such that channels 542 form an actual initial space for fluid flow. The actual initial space defined by channels 542 is closed off or sealed by distal seal 530 and proximal seal 531. Distal seal 530 is similar to distal seal 30 and is disposed at a distal end of body assembly 512. Proximal seal 531 is disposed at a proximal end of body assembly 512 and is formed by sealing the middle member 518 to the inner member 516 at the proximal ends thereof. Middle member 518 can include an outer layer of absorbent material 551, such as sponge, along one or more of the expandable portions 534 as shown in FIG. 17 for absorbing body fluids and/or cells. Where the middle member includes an outer layer, the outer layer can be made of or can include electrically conductive material for electrical coagulation or cautery.

Collars 520 are assembled on the assembly of middle member 518 and inner member 516 with a snug fit as shown in FIG. 16. Collars 520a and 520c are similar to collars 20 and have a straight tubular configuration with lumens allowing passage therethrough by the assembly of the middle member 518 and inner member 516. Collar 520b is similar to collars 520a and 520c except that collar 520b is angled or bent to have a non-straight configuration corresponding to the angled or bent configuration of inner member 516. The collar 520b has a proximal section 541 aligned with a longitudinal axis of the instrument 510 and a distal section 543 disposed at an angle with the collar proximal section 541 that is the same as the angle that inner member distal section 537 is disposed with inner member proximal section 535. The inner member 516 and the collar 520b can be rigidly bent or angled or the inner member 516 and one or more of the collars 520 can be made of a bendable material allowing the inner member 516 and the one or more collars 520 to be selectively bent, curved or angled during use in accordance with the procedure to be performed. Collars 520a, 520b and 520c define expandable portions 534 including a distal expandable portion 534a, an intermediate expandable portion 534b and a proximal expandable portion 534c with the distal and intermediate expandable portions 534a and 534b being angularly offset from proximal expandable portion 534c. With the collars 520 disposed on the assembly of middle member 518 and inner member 516, the tight fit of the collars 520 causes the middle member 51, which can fit tight or loose on inner member 516, to be held tight against the inner member 516, and the channels 542 couple the fluid supply system 546 with expandable portions 534 to allow fluid flow between the middle member 518 and the inner member 516 along, through or past the collars 520 to move expandable portions 534 between the expanded and non-expanded positions.

Head assembly 514 for multifunctional instrument 510 is similar to head assembly 14 except that valve assembly 548 for head assembly 514 is part of the supplemental inlet assembly 550. Handle 539 is similar to handle 39 except that handle 539 has a distally extending tubular neck or collar 545 for receiving a proximal end of the body assembly 512. Proximal ends of the inner member 516 and the middle member 518, respectively, are disposed in passage 552 of the handle 539 with proximal seal 531 disposed proximally of fluid supply passages 554 and 558. Fluid supply system 546 for instrument 510 includes fluid supply passages 554 and 558 extending through handle 539 and through the middle member 518 to communicate with channels 542, respectively. The fluid supply passages 554 and 558 include valves 556 and 560, respectively, for controlling the flow of fluid supplied to channels 542. Supplemental inlet assembly 550 is similar to supplemental inlet assembly 50 and includes tube 582 extending into the lumen 525 of the inner member 516 and a valve 562 for selectively opening and closing the lumen of the tube 582.

Hysteroscopic use of multifunctional instrument 510 is illustrated in FIG. 17. Expandable portions 534a and 534b in the non-expanded position, illustrated in FIG. 14, are introduced in the uterus U through the cervix C. Expandable portions 534a and 534b are positioned in the uterus U, and expandable portion 534c is positioned adjacent the external cervical os O with the proximal section 541 of collar 520b extending along the cervix C. Fluid is supplied via passages 554 and 558 to channels 542 to move the expandable portions 534 from the non-expanded position to the expanded position illustrated in FIG. 17. In the expanded position, expandable portion 534a has a size and shape corresponding substantially to the size and shape of the uterus U, expandable portion 534b has a size smaller than the size of expandable portion 534a to close off or seal the internal os O', and expandable portion 534c has a size larger than the size of expandable portion 534b and smaller than the size of expandable portion 534a to close off or seal the external cervical os O. Various fluids, medicaments and other instruments, such as a hysteroscope I, can be introduced at and/or withdrawn from the uterus U via the lumen 525 of inner member 516 and inlet assembly 550. The different sizes for expandable portions 534 in the expanded position can be obtained in various ways such as by varying the density or elasticity of the middle member 518, with the use of preformed expandable portions and/or by individual, controlled expansion of expandable portions 534 via channels 542 as explained further below. With the instrument 510, hysteroscopic and manipulating procedures can be conducted in the uterus with the cervix C closed off or sealed and the instrument 510 stabilized by expandable portions 534b and 534c. Fluid and tissue cell samples can be collected with the instrument 510 by contact of the fluid and tissue with absorbent material 551. Accordingly, fluid and tissue samples can be taken from areas of the body such as the uterus and cervix for uterine and endocervical cell collection. The angular configuration of instrument 510 is particularly useful for procedures involving a retroverted uterus. By making the middle member 518 and/or the absorbent layer 551 of electrically conductive material or by providing the middle member 518 and/or the absorbent layer 551 with electrically conductive fibers or a spine, the instrument 510 can be utilized to treat tissue with electrical energy, such as in electric coagulation or cautery, as is particularly useful in uterine ablation.

Figure 18:
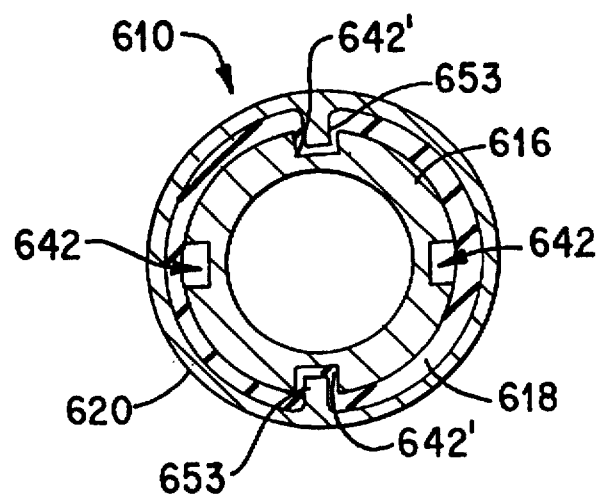
FIG. 18 is a cross-sectional view of an additional modification of an expandable multifunctional instrument according to the present invention.

Another modification of a multifunctional instrument according to the present invention is illustrated in FIG. 18 at 610. Multifunctional instrument 610 is similar to multifunctional instrument 510 except that inner member 616 for multifunctional instrument 610 has two or more channels 642 and collars 620 for instrument 610 have one or more ridges or protrusions 653, less than the number of channels 642, for being received in one or more channels 642, one collar 620 being shown in FIG. 18. Inner member 616, which can be straight or angled, is similar to inner member 516 except that inner member 616 has four channels 642 extending longitudinally along an outer surface thereof at 90° spaced locations about a longitudinal axis of instrument 610. Middle member 618 is similar to middle member 518 and is in the nature of a tubular balloon for being assembled over the inner member 616 with a tight fit or with a loose fit. Collar 620 is similar to collars 520 except that collar 620 has two ridges or protrusions 653 extending longitudinally along an inner surface thereof at locations corresponding to the locations of two of the channels 642, the ridges 653 being arranged at 180° spaced locations about the instrument longitudinal axis to correspond to the locations of channels 642'. Ridges 653 have a configuration in cross-section for being cooperatively engaged in channels 642' when the collar 620 is assembled on the assembly of the middle member 618 and the inner member 616 with a tight fit. With the ridges 653 received in the channels 642', the middle member 618 will be moved into the channels 642' by the ridges 653. The remaining channels 642 that do not have ridges 653 therein define an actual initial space allowing fluid flow between the middle member 618 and the inner member 616 along the collar 620 for moving expandable portions of the instrument 610 between the non-expanded and the expanded positions. The collar 620 with one or more ridges 653 received in fewer than all of the channels 642 is particularly advantageous for facilitating controlled longitudinal movement or adjustment of the collar 620 along the assembly of the middle member 618 and the inner member 616 to adjust the length, location and separation distance of the expandable portions and for preventing rotation of the collar 620 where rotation of the collar 620 is not desired.

An additional modification of a multifunctional instrument according to the present invention is illustrated at 710 in FIG. 19. Multifunctional instrument 710 is similar to multifunctional instrument 610 except that collar 720 for instrument 710 fits loosely on the assembly of the middle member 718 and the inner member 716 such that all of the channels 742 can have ridges 753 received therein in cooperative engagement with the loose fit of the collar 720 permitting fluid flow between the middle member 718 and the inner member 716 to move expandable portions of the instrument 710 between the non-expanded and the expanded positions. As shown in dotted lines, additional channels 742 that do not have ridges 753 engaged therewith can be provided in the collar inner member 716 to further facilitate fluid flow. It will be appreciated that the distance that ridges 753 extend inwardly from the inner surface of collar 720 to engage channels 742 will vary in accordance with the size of the gap or space between the collar 720 and the inner member 716. With the instrument 710, the middle member 718 can be disposed over the inner member 716 with a tight fit as shown in FIG. 18, in which case a potential space will be defined between the middle member and the inner member, or with a loose fit, as shown in FIG. 19, in which case an actual initial space 740 will be defined between the middle member 718 and the inner member 716.

Figure 20:
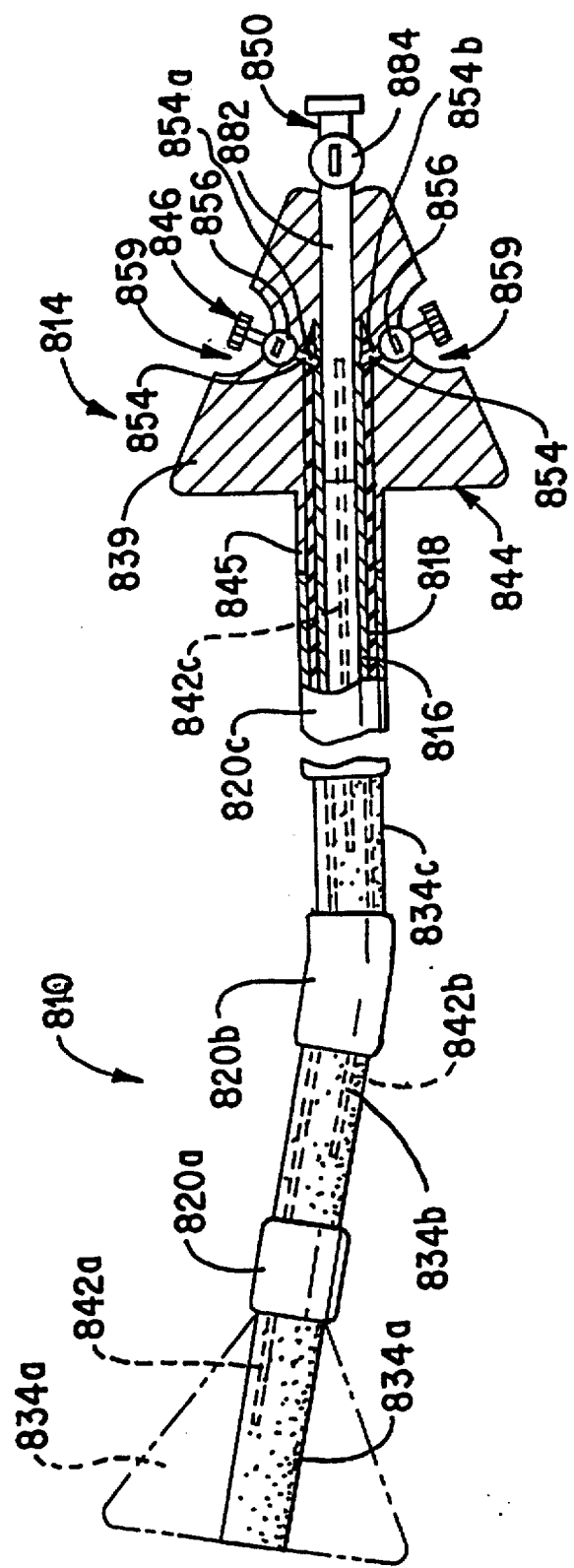
FIG. 20 is a broken side view, partly in section, of a further modification of an expandable multifunctional instrument according to the present invention.
Figure 21:
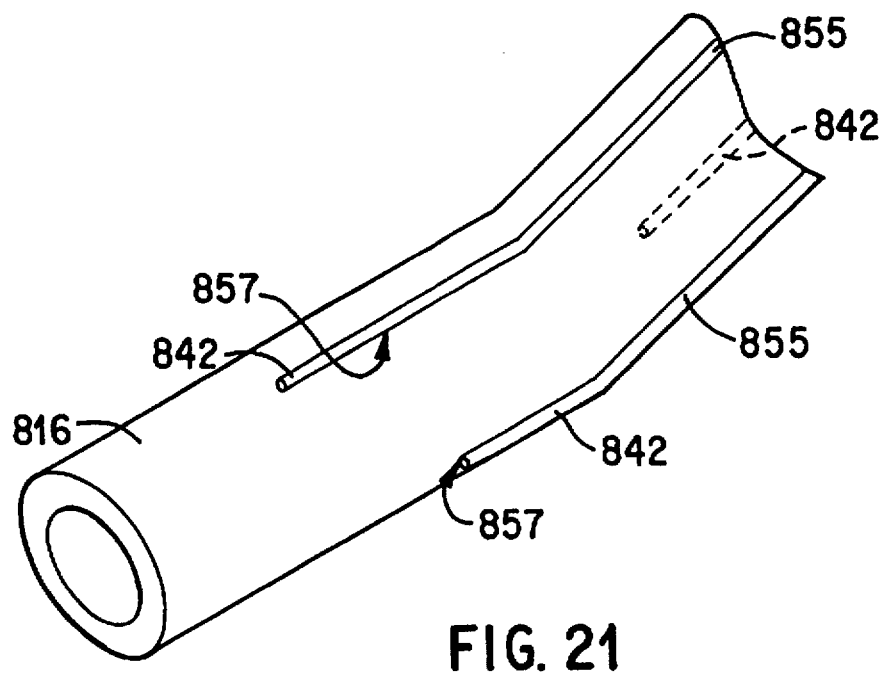
FIG. 21 is a broken perspective view of the inner member for the expandable multifunctional instrument of FIG. 20.

Another modification of a multifunctional instrument according to the present invention is illustrated in FIG. 20 at 810. Multifunctional instrument 810 is similar to multifunctional instrument 510 with the primary difference being that channels 842 of instrument 810 are closed along the outer surface of the inner member 816. As shown in FIG. 21, channels 842 extend longitudinally along the inner member 816 and are formed by tubes 855 secured along the outer surface of the inner member 816, within recesses 857 along the inner member outer surface or within the wall of the inner member 816. Instrument 810 includes middle member 818 disposed over inner member 816 and collars 820 disposed over the assembly of middle member 818 and inner member 816, three collars 820a, 820b and 820c being shown. Collars 820 define three expandable portions 834a, 834b and 834c with one of the channels 842 communicating with a respective one of the expandable portions 834 such that the channels 842 define actual initial spaces for fluid flow between the middle member 818 and the inner member 816. As shown in dotted lines in FIG. 20, channel 842a extends lengthwise to terminate at expandable portion 834a, channel 842b extends lengthwise to terminate at expandable portion 834b, and channel 842c extends lengthwise to terminate at expandable portion 834c for individual, controlled distension or expansion of expandable portions 834a, 834b and 834c as explained further below.

Head assembly 814 for instrument 810 includes handle assembly 844, fluid supply system 846 formed as part of handle assembly 844 and supplemental inlet assembly 850. Handle assembly 844 includes handle 839 having a conical configuration corresponding to the configuration of expandable portion 834a in the expanded position and/or corresponding to the shape or configuration of the anatomical cavity or organ in which the instrument 810 is to be introduced, the configuration of handle 839 corresponding to the configuration of the uterus and to the configuration of expandable portion 834a in the expanded position as shown in dotted lines in FIG. 20. Handle 839 has a neck 845 extending distally therefrom for receiving the proximal ends of inner member 816 and middle member 818. Fluid supply system 846 includes a plurality of fluid supply passages or conduits 854 having valves 856 mounted in recesses 859 in handle 839 to be in a safe, protected position. Three conduits are provided in instrument 810 for communicating with channels 842a, 842b and 842c, respectively, two conduits 854a and 854b being shown communicating with channels 842a and 842b with a third conduit (not shown) on an opposite side of handle 839 communicating with channel 842c. Supplemental inlet assembly 850 includes a tube 882 extending proximally from handle 839 and a valve 884 for controlling opening and closing of the lumen of tube 882. Use of instrument 810 is similar to that previously described except that expandable portions 834a, 834b and 834c can be selectively, individually moved between the expanded and non-expanded positions via the separate fluid supply paths formed by channels 842. The expandable portions 834 can thus be expanded or pressurized individually to control the size of the expandable portions in the expanded condition. The separate flow paths also permit selected expandable portions 834 to remain undistended or unexpanded depending on procedural use. Additionally, the separate flow paths provide redundant protection in that if an expandable portion should burst or leak, other expandable portions remain operable. Accordingly, where more than one expandable portion is introduced in an anatomical cavity and one of the expandable portions leak, bursts or otherwise malfunctions, another expandable portion is available with which to perform or complete the medical procedure.

Figure 22:
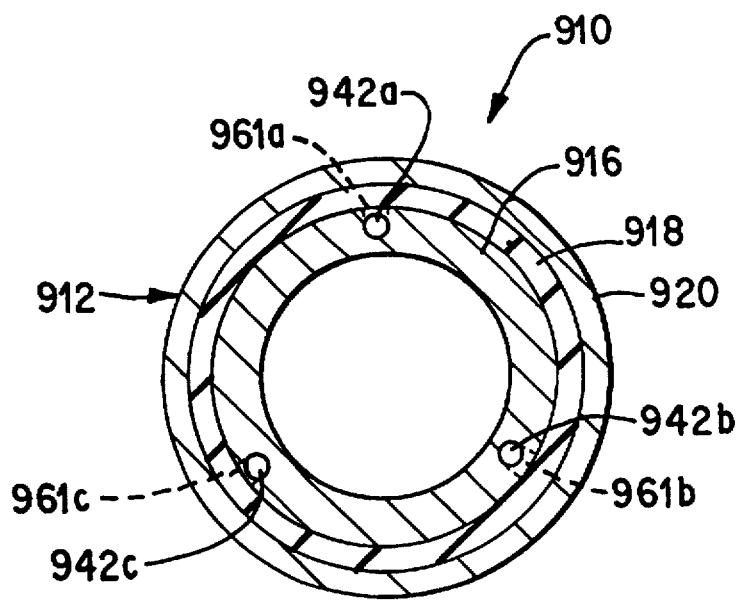
FIG. 22 is a cross-sectional view of another modification of an expandable multifunctional instrument according to the present invention.

A further modification of a multifunctional instrument according to the present invention is illustrated in FIG. 22 at 910. Multifunctional instrument 910 is similar to multifunctional instrument 810 except that channels 942 for instrument 910 are disposed within the wall of the inner member 916. Body assembly 912 for multifunctional instrument 910 includes inner member 916 received in middle member 918 and collar 920 disposed over the assembly of middle member 918 and inner member 916. Channels 942a, 942b and 942c are formed in the thickness of the wall forming inner member 916 and terminate at angled channel segments 961a, 961b and 961c communicating with a respective expandable portion of instrument 910 for controlled, individual distension of the expandable portions.

Figure 23:
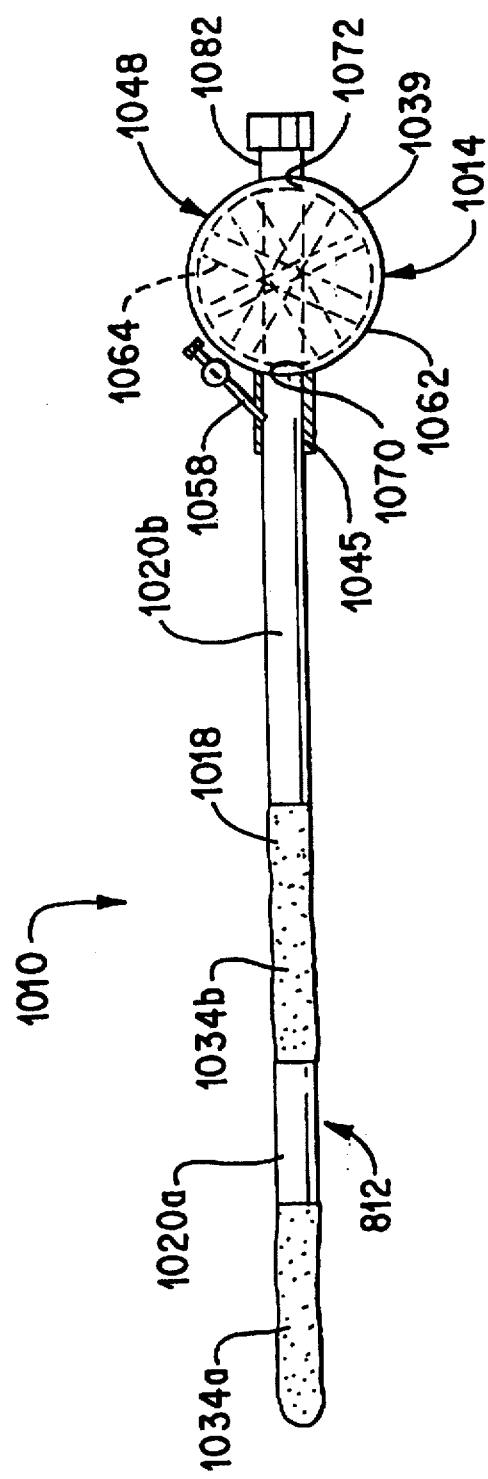
FIG. 23 is a broken side view of yet another modification of an expandable multifunctional instrument according to the present invention.

An additional modification of a multifunctional instrument according to the present invention is illustrated in FIG. 23 at 1010. Multifunctional instrument 1010 is similar to multifunctional instrument 10 except that middle member 1018 for instrument 1010 is made of an absorbent material, such as medical grade sponge, that distends, swells or increases in size upon absorption of fluids. The sponge forming middle member 1018 can be soft, or the sponge can be rough to have a brushing or scraping effect on tissue contacted thereby. The sponge can be made rough in many various ways such as by forming the sponge to include stiff fibers or wires or as a relatively stiff mesh or abrasive. Body assembly 1012 for multifunctional instrument 1010 includes middle member 1018 receiving an inner member 1016, shown in FIG. 24, and collars 1020a and 1020b disposed over the assembly of the middle member 1018 and the inner member 1016 for defining expandable portions 1034a and 1034b and for controlling, limiting or constraining distension or expansion of middle member 1018 upon absorption of fluids thereby. The middle member 1018 preferably has a size and configuration in a dry state prior to absorption of fluids such that expandable portions 1034 in a non-expanded position form a substantially uniform profile with collars 1020 to facilitate introduction through relatively small size anatomical openings. The middle member 1018 has a size in the wet state that is larger in size than the size of the middle member in the dry state such that expandable portions 1034 form enlargements or protrusions in an expanded position. The configuration and size of the expandable portions 1034 in the expanded position can be controlled in many various ways such as by varying the density of the absorbent material, varying the absorption characteristics of different portions of the middle member 1018 and with the use of mechanical spine members for guiding the expansion and/or configuration of the expandable portions 1034 in the expanded position. Collars 1020a and 1020b are similar to collars 20 except that collar 1020a is made of a bendable material allowing collar 1020a to be bent, angled or shaped manually prior to use.

Head assembly 1014 for multifunctional instrument 1010 includes valve assembly 1048 forming a handle 1039 and an inlet lumen for instrument 1010. Valve assembly 1048 is similar to valve assembly 48 and includes adjustable valve 1062 having a forward opening 1070 coupled with a proximal end of body assembly 1012. A tube 1082 is coupled with a rearward opening 1072 of valve 1062 in alignment with the lumen of the inner member allowing instruments to be introduced therethrough upon alignment of one of the valve passages 1064 with the openings 1070 and 1072. A neck 1045 extends distally from valve 1062 for receiving a proximal end of body assembly 1012, and a passage or conduit 1058 extends through neck 1045 to communicate with the middle member 1018 for aspiration of body fluids therefrom to facilitate withdrawal of the instrument 1010 via the anatomical opening. It should be appreciated that expandable portions 1034 are moved to the expanded position by contact with or absorption of body fluids such that a separate fluid supply system and distal and proximal seals are not required; however, the expandable portions can also be moved between the non-expanded and expanded positions via fluid supplied to sponge 1018 in which case head assembly 1014 can include a supply system.

Figure 24:
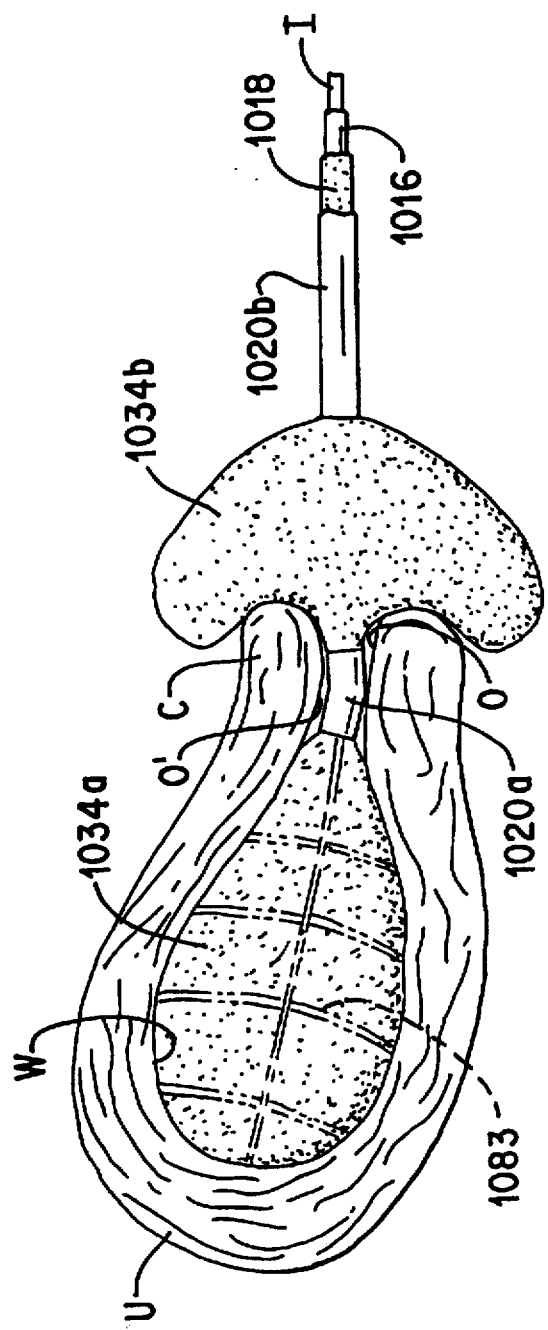
FIG. 24 is a broken side view of the expandable multifunctional instrument of FIG. 23 during use with the expandable portions in the expanded position.

Use of multifunctional instrument 1010 is similar to that previously described; however, prior to introduction of a distal end of body assembly 1012 in an anatomical cavity, collar 1020a is manually bent or angled in accordance with the anatomical characteristics of the patient and/or procedural use. The distal end of body assembly 1012 is then introduced in the anatomical cavity, such as the uterus U, via a relatively small size anatomical opening such as the cervix C, with the expandable portions 1034 in the non-expanded position shown in FIG. 23. Expandable portion 1034a is positioned in the uterus U and expandable portion 1034b is positioned externally adjacent the external cervical os O with collar 1020a extending along the cervix C. Upon absorption of body fluids by middle member 1018, expandable portions 1034 are moved from the non-expanded position to the expanded position forming enlargements or protrusions, as illustrated in FIG. 24, with distension or expansion of the middle member 1018 being constrained along collars 1020. In the expanded position, the expandable portion 1034a fills and conforms to the size and shape of the uterus U to touch the entire or substantially the entire uterine wall W, and expandable portion 1034b is caused by the vaginal walls to envelop or cup the cervix C. In the expanded position, expandable portions 1034a and 1034b close off or seal the internal cervical os O' and the external cervical os O, respectively, and also stabilize the instrument 1010. Various instruments, such as a hysteroscope I, can be introduced in the anatomical cavity via the valve assembly 1048 and the lumen of the inner member. Various tissue and fluid samples can be collected via absorption by middle member 1018. Body fluids absorbed by middle member 1018 can be aspirated through conduit 1058 to move the expandable portions to the non-expanded position or to reduce the size of distended expandable portions 1034 to facilitate withdrawal of instrument 1010 from the body. Multifunctional instrument 1010 is particularly advantageous for performing endometrial ablation to treat, for example, dysfunctional uterine bleeding in that an electrically conductive spine 1083, shown in dotted lines in FIG. 24, can be disposed within or on middle member 1018 for contacting anatomical tissue to form an electrosurgical device for coagulating large surface areas, such as the endometrium of the uterus U, as disclosed in applicant's prior application Ser. No. 07/600,775 filed Oct. 23, 1990, the disclosure of which is incorporated herein by reference. It should also be appreciated that various mechanical spine members can be utilized to move the expandable portions 1034 between the non-expanded and expanded positions and that expandable portions 1034 can be provided within an external resilient, stretchable or elastic membrane.

FIG. 25 illustrates at 1110 a further modification of an expandable multifunctional instrument according to the present invention. Body assembly 1112 for multifunctional instrument 1110 includes inner member 1116, middle member 1118 receiving inner member 1116, a collar 1120 disposed around middle member 1118 and an expandable spine 1183 for mechanically shaping and/or expanding the middle member 1118. Spine 1183 can be part of the inner member 1116 or the middle member 1118, or the spine can be a separate component disposed between the inner member 1116 and the middle member 1118. As shown for instrument 1110, spine 1183 is part of the inner member 1116, which is similar to inner member 16. Inner member 1116 carries expandable spine 1183 including a plurality of legs 1192 pivotally or hingedly attached to the inner member 1116 at pivots, joints or hinges. Legs 1116 can be pivotally attached to the inner member 1116 at various locations in accordance with the configuration desired for expandable portion 1134 in the expanded position; and, as shown for instrument 1110, legs 1116 are equally spaced about a longitudinal axis of the instrument. Spine 1183 is biased to or normally disposed in an expanded position wherein the legs 1192 are disposed angularly outwardly of the inner member 1116 and the longitudinal axis of the instrument 1110 as shown in FIG. 26. In the expanded position, spine 1183 has a predetermined configuration depending on the medical procedure to be performed, the spine 1183 having a predetermined triangular or conical configuration in the expanded position advantageous for uterine use. Spine 1183 can be biased to or normally disposed in the expanded position in many various ways including an integral spring bias or with a separate spring component. Spine 1183 can be formed integrally, unitarily with inner member 1116 or separately therefrom. As shown for instrument 1110, legs 1192 are formed integrally, unitarily with a distal end of inner member 1116 and are biased outwardly by an integral spring bias. If desired, the legs 1192 can have curved distal tips 1193 for smoothly contouring middle member 1118. Spine 1183 is movable by collar 1120 from the expanded position to a non-expanded or collapsed position shown in FIG. 25 wherein the legs 1192 have a configuration to fit within collar 1120. In the non-expanded position for spine 1183, legs 1192 are disposed within collar 1120 parallel or substantially parallel with the longitudinal axis of instrument 1110.

Spine 1183 is normally angularly offset from inner member 1116 to be normally disposed at an angle with the instrument longitudinal axis and to be movable by collar 1120 to an aligned position with inner member 1116 to fit within collar 1120. Accordingly, in the normal offset position as shown in FIG. 27, a longitudinal axis of spine 1183 is disposed at an angle with a longitudinal axis of inner member 1116 and, therefore, with the instrument longitudinal axis. In the aligned position shown in FIGS. 25 and 26, the longitudinal axis of spine 1183 is longitudinally aligned with the longitudinal axis of inner member 1116 and therefore, the longitudinal axis of instrument 1110. Spine 1183 and/or the inner member 1116 can be designed in many various ways to provide spine 1183 with a normal predetermined or variable offset or angular position. As shown for instrument 1110, inner member 1116 includes a resilient, flexible, bendable or deformable segment or neck 1194 proximally adjacent spine 1183. Segment 1194 has a predetermined bend, curve or angle to normally position or bias spine 1183 to the offset position while allowing movement of segment 1194 by collar 1120 to position spine 1183 in the aligned position.

Middle member 1118 includes a transparent stretchable or elastic membrane or a non-elastic or rigid preformed membrane having an end wall 126 at the distal end thereof forming a distal seal 1130 closing off or sealing the lumen of the middle member. Middle member 1118 is disposed over inner member 1116 with spine 1183 disposed in middle member 1118 to define expandable portion 1134 along the length of legs 1192. Middle member 1118 extends proximally from distal end wall 1126 to terminate at a proximal flange 1128 mounted to head assembly 1114.

Collar 1120 is similar to collar 20 and terminates distally at a forward edge 1136 and proximally at a proximal flange 1195 mounted to head assembly 1114. Flange 1195 has a peripheral configuration corresponding to the inner configuration of operating member 1196 of head assembly 1114 with an external thread or teeth 1197 for mating with an internal thread or teeth 1197' of operating member 1196 as explained further below.

Head assembly 1114 includes handle 1139 mounting the inner member proximal end 1124, operating member 1196 mounting the middle member proximal flange 1128 and the collar proximal flange 1195 and a valve assembly 1148. Handle 1139 has a configuration indicative of the configuration of expandable portion 1134 in the expanded position and/or the anatomical cavity in which the instrument 1110 is designed to be used. Inner member 1116 extends through handle 1139 to terminate at valve assembly 1148 and can be secured to handle 1139 in many various ways including adhesively or with the use of detents. Valve assembly 1148 is disposed in a recess of handle 1139 to be in a protected condition and can include any suitable valve for selectively opening and closing the lumen 1125 of inner member 1116 to control the flow of fluid and/or the passage of instruments therethrough.

Operating member 1196 is disposed distally of handle 1139 and includes a cylinder having a rear wall 1198 and a forward wall 1199. Rear wall 1198 has a recess therein for receiving flange 1128 of middle member 1118 and an opening allowing passage therethrough of inner member 1116. The middle member 1118 can be proximally sealed to the inner member 1116 at flange 1128 or at any other desirable location. The forward wall 1199 of operating cylinder 1196 has an opening therein allowing passage therethrough of the collar 1120 such that the collar flange 1195 is disposed in cylinder 1196 with teeth or thread 1197 of flange 1195 in mating engagement with teeth or thread 1197' of cylinder 1196. Thread 1197' extends the entire length of cylinder 1196 to permit movement of collar 1120 distally and proximally in response to rotation of cylinder 1196 relative to body assembly 1112. The inner surface of collar 1120 can be made of a slippery material and/or the middle member 1118 can be made of a tear resistant material to facilitate movement of collar 1120 along middle member 1118.

Prior to introduction in an anatomical cavity, the expandable portion 1134 is disposed in collar 1120 to be in the non-expanded position shown in FIG. 25 with collar flange 1195 at a forward end of operating cylinder 1196. Spine 1183 is maintained by collar 1120 in both the collapsed position and the aligned position to facilitate introduction of the distal end of body assembly 1112 through a small size anatomical opening. With expandable portion 1134 in the non-expanded, aligned position, the distal end of body assembly 1112 is introduced through the anatomical opening. Once the distal end of body assembly 1112 is positioned in the anatomical cavity, operating cylinder 1196 is manually rotated while gripping handle 1139 causing longitudinal proximal movement of collar 1120 via teeth 1197 and 1197'. As shown in FIG. 26, operating cylinder 1196 is rotated until forward edge 1136 of collar 1120 is disposed proximally of expandable portion 1134 causing spine 1183 to move automatically to the expanded position with legs 1192 disposed in a direction angularly outwardly of the instrument longitudinal axis as shown in FIG. 26. Movement of spine 1183 to the expanded position causes movement of expandable portion 1134 to the expanded position forming an enlargement or protrusion between end wall 1126 and collar forward edge 1136. If desired, fluid can be supplied to expandable portion 1134 via valve assembly 1148 and the lumen 1125 of inner member 1116 to further shape or maintain the shape of or to increase the size of expandable portion 1134 in the expanded position. In the expanded position, the expandable portion 1134 can be used to manipulate tissue or organ structure in the anatomical cavity for various medical procedures.

When it is desired to change the direction or orientation of expandable portion 1134, operating cylinder 1196 is further rotated manually to move collar 1120 further proximally along the assembly of middle member 1118 and inner member 1116 as shown in FIG. 27 until collar flange 1195 is disposed in abutment with rear wall 1198 of operating cylinder 1196. Accordingly, collar forward edge 1136 will have moved proximally exposing all or a portion of segment 1194, the forward edge 1136 being disposed approximately at the mid-point of segment 1194 in FIG. 27. Exposure of segment 1194 distally beyond collar forward edge 1136 causes segment 1194 to assume the predetermined bend thusly moving spine 1183 and, therefore, expandable portion 1134 to the offset position. With the expandable position 1134 in the expanded, offset position, access to tissue or organ structure as well as manipulation thereof is greatly facilitated.

FIGS. 28A–28D illustrate in side view alternative predetermined configurations for the expandable portions of the multifunctional instruments according to the present invention in the expanded position. The various predetermined side view configurations illustrated in FIGS. 28A–28D can be utilized-with various types of middle or distensible members including an elastic middle member, a preformed rigid middle member, a middle member with surrounding absorbable layer and an absorbable material middle member, for example.

Figure 28A:
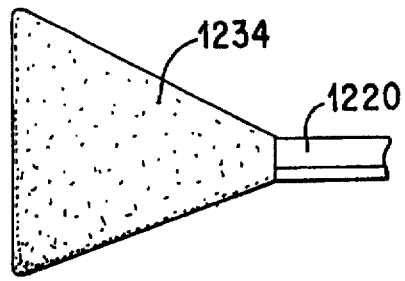
FIGS. 28A–28D illustrate alternative configurations in side view for the expandable portions of the multifunctional instruments according to the present invention in the expanded position.

As illustrated in FIG. 28A, expandable portion 1234 in the expanded position has a predetermined triangular or fan-shaped configuration in side view adjacent collar 1220. The triangular configuration of expandable portion 1234 is advantageous for universal use and, in particular, for use in uterine and kidney procedures and in the retroperitoneal space.

Figure 28B:
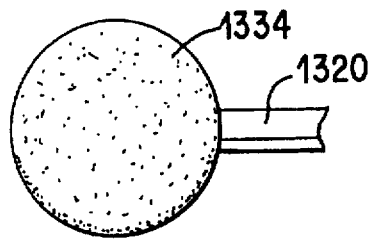

FIG. 28B illustrates an expandable portion 1334 having a predetermined round or circular configuration in side view in the expanded position adjacent collar 1320. When the expandable portion 1334 also has the predetermined end view configuration of FIG. 29A, the instrument is particularly useful for lysis of adhesions and in the uterovesical pouch.

Figure 28C:
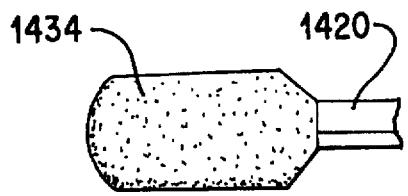

FIG. 28C illustrates an expandable portion 1434 in the expanded position adjacent collar 1420 and having a predetermined oblong configuration in side view with a convex forward end and a truncated triangular rearward end tapering to collar 1420 with a longitudinal axis of the expandable portion 1434 aligned with a longitudinal axis of collar 1420. Expandable portion 1434 is particularly advantageous for use in deep channels, the retroperitoneal space and areas that cannot be visualized, and the configuration of expandable portion 1434 is particularly desirable for fitting through internal channels.

Figure 28D:
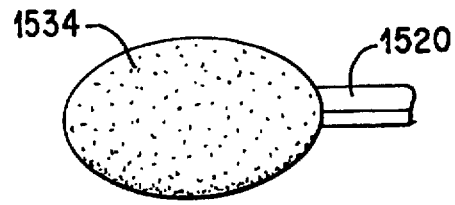

FIG. 28D shows an expandable portion 1534 in the expanded position adjacent collar 1520, the expandable portion 1534 having a predetermined oval or elliptical configuration in side view. Expandable portion 1534 is particularly advantageous for universal use when configured as shown in FIG. 29A and for use in cupping and/or manipulating or lifting free floating organ structure such as the gall bladder and ovary when configured as shown in FIG. 29B.

Figure 29A:
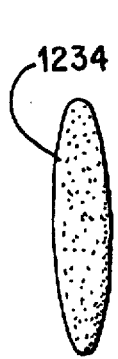
FIGS. 29A–29E illustrate alternative configurations in end view for the expandable portions of FIGS. 28A–28D.

FIGS. 29A–29E illustrate predetermined end view configurations for any of the expandable portions of FIGS. 28A–28D in the expanded position. FIG. 29A illustrates expandable portion 1234 of FIG. 28A in end view wherein the expandable portion 1234 has a relatively narrow oval predetermined configuration such that the overall configuration of the expandable portion is that of a flattened cone advantageous for universal use, in uterine and kidney procedures and in the retroperitoneal space. Where the expandable portion 1334 of FIG. 28B has the predetermined end view configuration of FIG. 29A, the instrument is particularly advantageous for lysis of adhesions and in the uterovesical pouch.

Figure 29B:
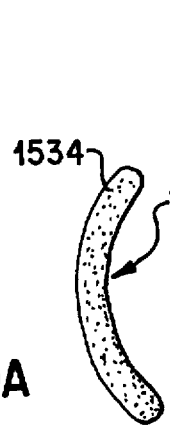

FIG. 29B illustrates a predetermined cup, arcuate or crescent shape configuration in end view for the expandable portions, as shown for the expandable portion 1534 of FIG. 28D. The cup shape configuration of FIG. 29B defines a recess 1600 for accommodating tissue or organ structure and is particularly useful in bowel and gallbladder procedures and for supporting tissue or organ structure in a cupping manner and/or for lifting tissue or organ structure.

Figure 29C:
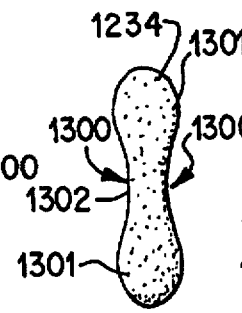

FIG. 29C illustrates in end view a predetermined dumbbell shape for the expandable portions, as shown for expandable portion 1234 of FIG. 28A. As shown in FIG. 29C, expandable portion 1234 forms a pair of enlargements 1301 connected by a relatively narrow, central neck 1302 to define recesses 1300 for accommodating tissue or organ structure. The dumbbell configuration of FIG. 29C is especially desirable for lysis of adhesions, for spleen and pancreas procedures and for fitting between organs.

Figure 29D:
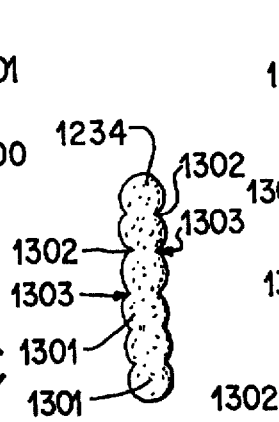

The end view configuration of FIG. 29D is illustrated for expandable portion 1234. The end view configuration of FIG. 29D is similar to the end view configuration of FIG. 29A except that the expandable portion 1234 forms a plurality of enlargements, protuberances or nodes 1301 connected by narrow necks 1302. The protuberances 1301 have a rounded configuration with a cross-sectional size larger than the cross-sectional size of necks 1302 to define a plurality of troughs 1303. The predetermined configuration of FIG. 26D is particularly useful in allowing drainage along the troughs 1303 such as in the case of a ruptured bowel.

Figure 29E:
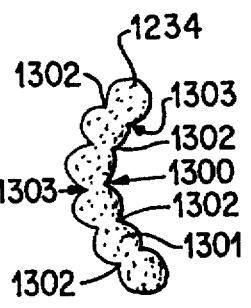

The predetermined end view configuration of FIG. 29E is similar to the end view configuration of FIG. 29D except that the expandable portion 1234 of FIG. 29E has an arcuate, spoon or cup shape defining recess 1300 for accommodating tissue or organ structure. Accordingly, in addition to permitting drainage along the troughs 1303, the expandable portion 1234 of FIG. 29E is useful for supporting or lifting tissue or organ structure in recess 1300 in a cupping manner such as is useful in bowel and gall bladder procedures.

The instruments according to the present invention utilize balloons for manipulating tissue for many purposes; and, while the instruments desirably have more than one function, the instruments can be designed to have a single, dedicated function. By utilizing multiple tubular members, irrigation and/or aspiration (suction) can be achieved through the inner member, spaces between members or via additional instruments introduced through the inner member, such additional instruments also providing functions such as a cauterizing, penetrating and/or cutting with or without accompanying suction to remove cut tissue and fluids. The balloons can be carried by instruments inserted into the anatomical cavity through sleeves or along with the sleeves, such as on a safety shield, as well as by the sleeves, as disclosed in parent patent applications Ser. No. 07/596, 937 and Ser. No. 07/222,776. The balloons can be inflated prior to manipulation of tissue or as part of the step of manipulating organ structures and are, thus, useful in moving organ structures by contact, separating adhered or non-adhered organ structures, elevating or spacing one organ structure relative to another and displacing the anatomical cavity wall from underlying organ structures, for example the abdominal wall during laparoscopy.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of performing an operative procedure in an anatomical cavity comprising the steps of introducing a distal end of a distensible member of a multifunctional medical instrument in the anatomical cavity through a relatively small size opening in a wall of the anatomical cavity with the distensible member in a non-distended position facilitating introduction of the distensible member through the opening;

moving the distensible member from the non-distended position to a distended position to increase the cross-sectional size of the distensible member between the distal end and a proximal end of the distensible member;

constraining selected longitudinally spaced portions of the distensible member between the distal and proximal ends to prevent movement of the selected portions to the distended position to selectively contour the distensible member to have a plurality of longitudinally spaced protuberances for engaging anatomical tissue in accordance with the operative procedure to be performed; and performing an operative procedure in the anatomical cavity with the multifunctional instrument with the distensible member in the distended position.

2. A method of performing an operative procedure as recited in claim 1 wherein said step of performing includes introducing medical instruments in the anatomical cavity through the distensible member.

3. A method of performing an operative procedure as recited in claim 2 and further including stabilizing the multifunctional instrument relative to the anatomical cavity with the distensible member in the distended position to stabilize instruments introduced through the lumen.

4. A method of performing an operative procedure as recited in claim 1 wherein said step of performing includes manipulating anatomical tissue with the distensible member in the distended position.

5. A method of performing an operative procedure as recited in claim 1 wherein said step of performing includes separating adhering tissue with the distensible member in the distended position.

6. A method of performing an operating procedure as recited in claim 1 wherein the distensible member includes a balloon and said moving step includes inflating the balloon.

* * * * *